US008623383B2

(12) United States Patent
Ching

(10) Patent No.: US 8,623,383 B2
(45) Date of Patent: Jan. 7, 2014

(54) RECOMBINANT ANTIGENS FOR DIAGNOSIS AND PREVENTION OF SPOTTED FEVER RICKETTSIAE

(75) Inventor: Wei-Mei Ching, Bethesda, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 459 days.

(21) Appl. No.: 12/480,290

(22) Filed: Jun. 8, 2009

(65) Prior Publication Data

US 2009/0304731 A1 Dec. 10, 2009

Related U.S. Application Data

(60) Provisional application No. 61/059,382, filed on Jun. 6, 2008.

(51) Int. Cl.

| | |
|---|---|
| ***A61K 39/02*** | (2006.01) |
| ***A61K 39/00*** | (2006.01) |
| ***A61K 38/00*** | (2006.01) |
| ***C07K 1/00*** | (2006.01) |
| ***G01N 33/554*** | (2006.01) |
| ***G01N 33/53*** | (2006.01) |

(52) U.S. Cl.

USPC .................. 424/234.1; 424/190.1; 424/184.1; 514/1.1; 530/300; 530/350; 530/825; 530/806; 435/7.1; 435/7.32

(58) Field of Classification Search

None

See application file for complete search history.

(56) References Cited

PUBLICATIONS

Fournier et al. Int. J. Syst. Bacteriol. 48:839-849, 1998.*

Sumner et al. protection of guniea pigs from experimental Rocky Mountain spotted fever by immunization with baculovirus expressed *Rickettsia rickettsii* rOmpA protein. IN: Vaccine Jan. 1995; vol. 13 No. 1 pp. 29-35. Especially abstract, p. 30 rigth col paras 3-4, p. 31 left col. para 3, p. 32 right col. para 3.

Anderson et al. "A Protective Protein Antigen of *Rickettsia rickettsii* Has Tandemly Repeated, Near-Identical Sequences" IN: Infect. Immun.; Sep. 1990; vol. 58, No. 9; p. 2760-2769.

* cited by examiner

*Primary Examiner* — S. Devi

(74) *Attorney, Agent, or Firm* — Ning Yang; Albert M. Churilla; Joseph K. Hemby

(57) ABSTRACT

The invention relates to the construction of recombinant, immunodominant polypeptides against spotted fever group *Rickettsia*. The invention also relates to a method for the use of the recombinant proteins, either singly or in combination, in detection and diagnostic assays of spotted fever. The proteins can also be used to induce immune response against spotted fever group *Rickettsia*.

11 Claims, 8 Drawing Sheets

FIG. 1 pOmpA_R.slovaca_
LDSALVLSNLTGVGVNNILLAADLVAPGADEGTVVFNGGVNGLNIGSNVAGTARNIGDGG 60
pOmpA_R.honei_
LDSALVLSNLTGVGVNNILLAADLVAPGADEGTVVFNGGVNGLNIGSNVAGTARNIGDGG 60
OmpA-X_R.rickettsii_
RDSVLVLSNLTGVGVNNILLAADLVAPGADEGTVVFNGGVNGLNVGSNVAGTARNIGDGG 60
pOmpA_R.peacockii_
LDSVLVLSNLTGVGVNNILLAADLVAPGADEGTIVFNGGVNGLNIGSNVAGTARNIGDGG 60
pOmpA_R.parkeri_
LDSGLVLSNLTGVGVNNILLAADLVAPGADEGTVIFNGGVNGLNIGSNVAGTARNIGDGG 60 pOmpA_R.slovaca_
GNKFNTLLIYNAVTITDDVNLEGIQNVLINNNADFTSSTAFNAGAIQINDATYTIDANNG 120
pOmpA_R.honei_
GNKFNTLSIYNAVTITDDVNLEGIQNVLINDNADFTSSTAFNAGTIQIKDATYTIDANNG 120
OmpA-X_R.rickettsii_
GNKFNTLLIYNAVTITDDVNLEGIQNVLINKNADFTSSTAFNAGAIQINDATYTIDANNG 120
pOmpA_R.peacockii_
GNKFNTLLIYNAVTITDDVNLEGIQNVLINNNADFTSSTAFNAGAIQINDATYTIDANNG 120
pOmpA_R.parkeri_
GNKFNTLLIDNAVTITDDVNLEGIQNVLINNKADFTSSTAFNAGAIQINDATYTIDANNG 120 pOmpA_R.slovaca_
NLNIPAGNIQFAHADAQLILQNSSGNDRTITLGANIDPDNDDEGIVILNSVTAGKKLTIA 180
pOmpA_R.honei_
NLNIPAGNIQFAHADAQLILQNSSGNDRTITLGANIDPDNDDEGIVILNSVTAGKKLTIA 180
OmpA-X_R.rickettsii_
NLNIPAGNIQFAHADAQLVLQNSSGNDRTITLGANIDPDNDDEGIVILNSVTAGKKLTIA 180
pOmpA_R.peacockii_
NLNIPAGNIQFAHADAQLVLQNSSGNDRTITLGANIDPDNDDEGIVILNSVTAGKKLTIA 180
pOmpA_R.parkeri_
NLNIPAGNIQFAHADAQLILQNSSGNDRTITLGANIDPDNDDEGIVILNSVTAGKKLTIA 180 pOmpA_R.slovaca_
GGKTFGGAHKLQTIVFKGAGDCGAAGTTFNTTNIELNITGQLELGATTANVVLFNDAVQL 240
pOmpA_R.honei_
GGKMFGGAHKLQTIVFKGAGNCGAAGTTFNTTNIVLDITGQLELGATTASVVLFNDAVQL 240
OmpA-X_R.rickettsii_
GGKTFGGAHKLQTILFKGAGDCSTAGTTFNTTNIVLDITGQLELGATTANVVLFNDAVQL 240
pOmpA_R.peacockii_
GGKTFGGAHKLQTILFKGAGDCSAAGTTFNTTNIVLDITGQLELGATTANVVLFNDAVQL 240
pOmpA_R.parkeri_
GGKTFGGAHKLQTIVFKGAGDCGTAGTTFNTTNIVLDITGQLELGATTANVVLFKDAVQL 240 pOmpA_R.slovaca_ TQ 242
pOmpA_R.honei_ TQ 242
OmpA-X_R.rickettsii_ TQ 242
pOmpA_R.peacockii_ TQ 242
pOmpA_R.parkeri_ TQ 242

FIG. 2 pOmpA_R.honei_
VTATSFVANSATINFGNSLAFNSNITGSGTTLTLGANQVTYTGTGSFTDTLTLNTTFDGA 60
pOmpA_R.conorii_
VTATSFVANSATINFGNSLAFNSNITGSGTTLTLGANQVTYTGTGSFTDTLTLNTTFDGA 60
pOmpA_R.slovaca_
VTATSFVANSATINFGNSLAFNSNITGSGTTLTLGANQVTYTGTGSFTDTLTLNTTFDGA 60
pOmpA_R.parkeri_
VTATSFVANSATINFGNSLAFNSNITGSGTTLTLGANQVTYNGTGSFTDTLTLNTTFDGA 60
OmpA-Y_R.rickettsii_
VTATSFVANSATINFSNSLAFNSNITGGGTTLTLGANQVTYTGTGSFTDTLTLNTTFDGA 60 pOmpA_R.honei_
AKSGGNILIKSGSTLDLSGVSTLALVVTATNFDMNNISPDTKYTVISAETAGGLKPTPKE 120
pOmpA_R.conorii_
AKSGGNILIKSGSTLDLSGVSNLALVVTATNFDMNNISPDTKYTVISAETAGGLKPTPKE 120
pOmpA_R.slovaca_
AKSGGNILIKSGSTLDLSGVSTLALVVTATNFDMNNISPDTKYTVISAETAGGLKPTPKE 120
pOmpA_R.parkeri_
AKSGGNILIKSGSTLDLSGVSTLALVVTATNFDMNNISPDTKYTVISAETAGGLKPTPKE 120
OmpA-Y_R.rickettsii_
AKSGGNILIKSGSTLDLSGVSTLALVVTATNFDMNNISPDTKYTVISAETAGGLKPTSKE 120 pOmpA_R.honei_
NVKITINNDNRFVDFTFDASTLTLFAEDIAADVIDEDFAPGGPLANIPNAANIKKSLELM 180
pOmpA_R.conorii_
NVKITINNDNRFVDFTFDASTLTLFAEDIAAGVIDEDFAPGGPLANIPNAANIKKSLELM 180
pOmpA_R.slovaca_
NVKITINNDNRFVDFTFDASTLTLFAEDIAADVIDEDFAPGGPLANIPNAANIKKSLELM 180
pOmpA_R.parkeri_
NVKITINNDNRFVDFTFDASTLTLFAEDIAADVIDKDFAPGGPLANIPNAANIKKSLELM 180
OmpA-Y_R.rickettsii_
NVKITINNDNRFVDFTFDASTLTLFAEDIAADVIDGDFAPGGPLANIPNAANIKKSLELM 180 pOmpA_R.honei_
EDAPNGSDARQAFNNFGLMTPLQEADATTHLMQDVVKPSDTIAAVNNQVVASNISSNITA 240
pOmpA_R.conorii_
EDAPNGSDARQAFNNFGLMTPLQEADATTHLMQDVVKPSDTIAAVNNQVVASNISSNITA 240
pOmpA_R.slovaca_
ADAPNGSDARQAFNNFGLMTPLQEADATTHLMQDVVKPSDTIAAVNNQVVASNISSNITA 240
pOmpA_R.parkeri_
GDAPNGSDARQAFNNFGLMTPLQEADATTHLMQDVVKPSDTIAAVNNQVVASNISSNITA 240
OmpA-Y_R.rickettsii_
EDAPNGSDARQAFNNFGLMTPLQEADATTHLIQDVVKPSDTIAAVNNQVVASNISSNITA 240 pOmpA_R.honei_ LNARMDKVQA 250
pOmpA_R.conorii_ LNARMDKVQA 250
pOmpA_R.slovaca_ LNARMDKVQA 250
pOmpA_R.parkeri_ LNARMDKVQV 250

SEQUENCE LISTING

```
<160> NUMBER OF SEQ ID NOS: 22

<210> SEQ ID NO 1
<211> LENGTH: 2249
<212> TYPE: PRT
<213> ORGANISM: Rickettsia rickettsii
<220> FEATURE:
<221> NAME/KEY: MISC_FEATURE
<223> OTHER INFORMATION: OmpA Open Reading Frame

<400> SEQUENCE: 1

Met Ala Asn Ile Ser Pro Lys Leu Phe Lys Lys Ala Ile Gln Gln Gly
1               5                   10                  15

Leu Lys Ala Ala Leu Phe Thr Thr Ser Thr Ala Ala Ile Met Leu Ser
            20                  25                  30

Ser Ser Gly Ala Leu Gly Val Ala Thr Gly Val Ile Ala Thr Asn Asn
        35                  40                  45

Asn Ala Ala Phe Ser Asn Asn Val Gly Asn Asn Asn Trp Asn Glu Ile
    50                  55                  60

Thr Ala Ala Gly Val Ala Asn Gly Thr Pro Ala Gly Gly Pro Gln Asn
65                  70                  75                  80

Asn Trp Ala Phe Thr Tyr Gly Gly Asp Tyr Thr Val Thr Ala Asp Ala
                85                  90                  95

Ala Asp Arg Ile Ile Lys Ala Ile Asn Val Ala Gly Thr Thr Pro Val
            100                 105                 110

Gly Leu Asn Ile Thr Gln Asn Thr Val Val Gly Ser Ile Ile Thr Lys
        115                 120                 125

Gly Asn Leu Leu Pro Val Thr Leu Asn Ala Gly Lys Ser Leu Thr Leu
    130                 135                 140

Asn Gly Asn Asn Ala Val Ala Ala Asn His Gly Phe Asp Ala Pro Ala
145                 150                 155                 160

Asp Asn Tyr Thr Gly Leu Gly Asn Ile Ala Leu Gly Gly Ala Asn Ala
                165                 170                 175

Ala Leu Ile Ile Gln Ser Ala Ala Pro Ser Lys Ile Thr Leu Ala Gly
            180                 185                 190

Asn Ile Asp Gly Gly Gly Ile Ile Thr Val Lys Thr Asp Ala Ala Ile
        195                 200                 205

Asn Gly Thr Ile Gly Asn Thr Asn Ala Leu Ala Thr Val Asn Val Gly
    210                 215                 220

Ala Gly Thr Ala Thr Leu Gly Gly Ala Val Ile Lys Ala Thr Thr Thr
225                 230                 235                 240

Lys Leu Thr Asn Ala Ala Ser Val Leu Thr Leu Thr Asn Ala Asn Ala
                245                 250                 255

Val Leu Thr Gly Ala Ile Asp Asn Thr Thr Gly Gly Asp Asn Val Gly
```

-continued

```
            260                 265                 270

Val Leu Asn Leu Asn Gly Ala Leu Ser Gln Val Thr Gly Asp Ile Gly
        275                 280                 285

Asn Thr Asn Ser Leu Ala Thr Ile Ser Val Gly Ala Gly Thr Ala Thr
    290                 295                 300

Leu Gly Gly Ala Val Ile Lys Ala Thr Thr Thr Lys Leu Thr Asp Ala
305                 310                 315                 320

Ala Ser Ala Val Lys Phe Thr Asn Pro Val Val Val Thr Gly Ala Ile
                325                 330                 335

Asp Asn Thr Gly Asn Ala Asn Asn Gly Ile Val Thr Phe Thr Gly Asn
            340                 345                 350

Ser Thr Val Thr Gly Asn Val Gly Asn Thr Asn Ala Leu Ala Thr Val
        355                 360                 365

Asn Val Gly Ala Gly Leu Leu Gln Val Gln Gly Gly Val Val Lys Ala
    370                 375                 380

Asn Thr Ile Asn Leu Thr Asp Asn Ala Ser Ala Val Thr Phe Thr Asn
385                 390                 395                 400

Pro Val Val Val Thr Gly Ala Ile Asp Asn Thr Gly Asn Ala Asn Asn
                405                 410                 415

Gly Ile Val Thr Phe Thr Gly Asn Ser Thr Val Thr Gly Asp Ile Gly
            420                 425                 430

Asn Thr Asn Ala Leu Ala Thr Val Asn Val Gly Ala Gly Thr Ala Thr
        435                 440                 445

Leu Gly Gly Ala Val Ile Lys Ala Thr Thr Thr Lys Leu Thr Asn Ala
    450                 455                 460

Ala Ser Val Leu Thr Leu Thr Asn Ala Asn Ala Val Leu Thr Gly Ala
465                 470                 475                 480

Ile Asp Asn Thr Thr Gly Gly Asp Asn Val Gly Val Leu Asn Leu Asn
                485                 490                 495

Gly Ala Leu Ser Gln Val Thr Gly Asn Ile Gly Asn Thr Asn Ser Leu
            500                 505                 510

Ala Thr Ile Ser Val Gly Ala Gly Thr Ala Thr Leu Gly Gly Ala Val
        515                 520                 525

Ile Lys Ala Thr Thr Thr Lys Leu Thr Asp Ala Ala Ser Ala Val Lys
    530                 535                 540

Phe Thr Asn Pro Val Val Val Thr Gly Ala Ile Asp Asn Thr Gly Asn
545                 550                 555                 560

Ala Asn Asn Gly Ile Val Thr Phe Thr Gly Asn Ser Thr Val Thr Gly
                565                 570                 575

Asp Ile Gly Asn Thr Asn Ser Leu Ala Thr Ile Ser Val Gly Ala Gly
            580                 585                 590

Thr Ala Thr Leu Gly Gly Ala Val Ile Lys Ala Thr Thr Thr Lys Leu
        595                 600                 605

Thr Asn Ala Ala Ser Val Leu Thr Leu Thr Asn Ala Asn Ala Val Leu
    610                 615                 620

Thr Gly Ala Ile Asp Asn Thr Thr Gly Gly Asp Asn Val Gly Val Leu
625                 630                 635                 640

Asn Leu Asn Gly Ala Leu Ser Gln Val Thr Gly Asp Ile Gly Asn Thr
                645                 650                 655

Asn Ser Leu Ala Thr Ile Ser Val Gly Ala Gly Thr Ala Thr Leu Gly
            660                 665                 670

Gly Ala Val Ile Lys Ala Thr Thr Thr Lys Ile Thr Asn Ala Val Ser
        675                 680                 685
```

-continued

```
Ala Val Lys Phe Thr Asn Pro Val Val Val Thr Gly Ala Ile Asp Ser
    690                 695                 700

Thr Gly Asn Ala Asn Asn Gly Ile Val Thr Phe Thr Gly Asn Ser Thr
705                 710                 715                 720

Val Thr Gly Asp Ile Gly Asn Thr Asn Ala Leu Ala Thr Val Asn Val
                725                 730                 735

Gly Ala Gly Thr Ala Thr Leu Gly Gly Ala Val Ile Lys Ala Thr Thr
            740                 745                 750

Thr Lys Leu Thr Asn Ala Ala Ser Val Leu Thr Leu Thr Asn Ala Asn
        755                 760                 765

Ala Val Leu Thr Gly Ala Ile Asp Asn Thr Thr Gly Gly Asp Asn Val
    770                 775                 780

Gly Val Leu Asn Leu Asn Gly Ala Leu Ser Gln Val Thr Gly Asp Ile
785                 790                 795                 800

Gly Asn Thr Asn Ser Leu Ala Thr Ile Ser Val Gly Ala Gly Thr Ala
                805                 810                 815

Thr Leu Gly Gly Ala Val Ile Lys Ala Thr Thr Thr Lys Leu Thr Asn
            820                 825                 830

Ala Ala Ser Val Leu Thr Leu Thr Asn Ala Asn Ala Val Leu Thr Gly
        835                 840                 845

Ala Val Asp Asn Thr Thr Gly Gly Asp Asn Val Gly Val Leu Asn Leu
    850                 855                 860

Asn Gly Ala Leu Ser Gln Val Thr Gly Asp Ile Gly Asn Thr Asn Ser
865                 870                 875                 880

Leu Ala Thr Ile Ser Val Gly Ala Gly Thr Ala Thr Leu Gly Gly Ala
                885                 890                 895

Val Ile Lys Ala Thr Thr Thr Lys Leu Thr Asn Ala Ala Ser Val Leu
            900                 905                 910

Thr Leu Thr Asn Ala Asn Ala Val Leu Thr Gly Ala Ile Asp Asn Thr
        915                 920                 925

Thr Gly Gly Asp Asn Val Gly Val Leu Asn Leu Asn Gly Ala Leu Ser
    930                 935                 940

Gln Val Thr Gly Asp Ile Gly Asn Thr Asn Ser Leu Ala Thr Ile Ser
945                 950                 955                 960

Val Gly Ala Gly Thr Ala Thr Leu Gly Gly Ala Val Ile Lys Ala Thr
                965                 970                 975

Thr Thr Lys Leu Thr Asp Ala Ala Ser Ala Val Lys Phe Thr Asn Pro
            980                 985                 990

Val Val Val Thr Gly Ala Ile Asp  Asn Thr Gly Asn Ala  Asn Asn Gly
        995                 1000                1005

Ile Val  Thr Phe Thr Gly Asn  Ser Thr Val Thr Gly  Asn Val Gly
    1010                1015                1020

Asn Thr  Asn Ala Leu Ala Thr  Val Asn Val Gly Ala  Gly Leu Leu
    1025                1030                1035

Gln Val  Gln Gly Gly Val Val  Lys Ala Asn Thr Ile  Asn Leu Thr
    1040                1045                1050

Asp Asn  Ala Ser Ala Val Thr  Phe Thr Asn Pro Val  Val Val Thr
    1055                1060                1065

Gly Ala  Ile Asp Asn Thr Gly  Asn Ala Asn Asn Gly  Ile Val Thr
    1070                1075                1080

Phe Thr  Gly Asn Ser Thr Val  Thr Gly Asn Val Gly  Asn Thr Asn
    1085                1090                1095

Ala Leu  Ala Thr Val Asn Val  Gly Ala Gly Leu Leu  Gln Val Gln
    1100                1105                1110
```

-continued

```
Gly Gly Val Val Lys Ala Asn Thr Ile Asn Leu Thr Asp Asn Ala
    1115                1120                1125

Ser Ala Val Thr Phe Thr Asn Pro Val Val Val Thr Gly Ala Ile
    1130                1135                1140

Asp Asn Thr Gly Asn Ala Asn Asn Gly Ile Val Thr Phe Thr Gly
    1145                1150                1155

Asn Ser Thr Val Thr Gly Asp Ile Gly Asn Thr Asn Ala Leu Ala
    1160                1165                1170

Thr Val Asn Val Gly Ala Gly Ile Thr Leu Gln Ala Gly Gly Ser
    1175                1180                1185

Leu Ala Ala Asn Asn Ile Asp Phe Gly Ala Arg Ser Thr Leu Glu
    1190                1195                1200

Phe Asn Gly Pro Leu Asp Gly Gly Gly Lys Ala Ile Pro Tyr Tyr
    1205                1210                1215

Phe Lys Gly Ala Ile Ala Asn Gly Asn Asn Ala Ile Leu Asn Val
    1220                1225                1230

Asn Thr Lys Leu Leu Thr Ala Ser His Leu Thr Ile Gly Thr Val
    1235                1240                1245

Ala Glu Ile Asn Ile Gly Ala Gly Asn Leu Phe Thr Ile Asp Ala
    1250                1255                1260

Ser Val Gly Asp Val Thr Ile Leu Asn Ala Gln Asn Ile Asn Phe
    1265                1270                1275

Arg Ala Arg Asp Ser Val Leu Val Leu Ser Asn Leu Thr Gly Val
    1280                1285                1290

Gly Val Asn Asn Ile Leu Leu Ala Ala Asp Leu Val Ala Pro Gly
    1295                1300                1305

Ala Asp Glu Gly Thr Val Val Phe Asn Gly Gly Val Asn Gly Leu
    1310                1315                1320

Asn Val Gly Ser Asn Val Ala Gly Thr Ala Arg Asn Ile Gly Asp
    1325                1330                1335

Gly Gly Gly Asn Lys Phe Asn Thr Leu Leu Ile Tyr Asn Ala Val
    1340                1345                1350

Thr Ile Thr Asp Asp Val Asn Leu Glu Gly Ile Gln Asn Val Leu
    1355                1360                1365

Ile Asn Lys Asn Ala Asp Phe Thr Ser Ser Thr Ala Phe Asn Ala
    1370                1375                1380

Gly Ala Ile Gln Ile Asn Asp Ala Thr Tyr Thr Ile Asp Ala Asn
    1385                1390                1395

Asn Gly Asn Leu Asn Ile Pro Ala Gly Asn Ile Gln Phe Ala His
    1400                1405                1410

Ala Asp Ala Gln Leu Val Leu Gln Asn Ser Ser Gly Asn Asp Arg
    1415                1420                1425

Thr Ile Thr Leu Gly Ala Asn Ile Asp Pro Asp Asn Asp Asp Glu
    1430                1435                1440

Gly Ile Val Ile Leu Asn Ser Val Thr Ala Gly Lys Lys Leu Thr
    1445                1450                1455

Ile Ala Gly Gly Lys Thr Phe Gly Gly Ala His Lys Leu Gln Thr
    1460                1465                1470

Ile Leu Phe Lys Gly Ala Gly Asp Cys Ser Thr Ala Gly Thr Thr
    1475                1480                1485

Phe Asn Thr Thr Asn Ile Val Leu Asp Ile Thr Gly Gln Leu Glu
    1490                1495                1500

Leu Gly Ala Thr Thr Ala Asn Val Val Leu Phe Asn Asp Ala Val
```

-continued

```
    1505                1510                1515

Gln Leu  Thr Gln Thr Gly Asn  Ile Gly Gly Phe Leu  Asp Phe Asn
    1520                1525                1530

Ala Lys  Asn Gly Met Val Thr  Leu Asn Asn Asn Val  Asn Val Ala
    1535                1540                1545

Gly Ala  Val Gln Asn Thr Gly  Gly Thr Asn Asn Gly  Thr Leu Ile
    1550                1555                1560

Val Leu  Gly Ala Ser Asn Leu  Asn Arg Val Asn Gly  Ile Ala Met
    1565                1570                1575

Leu Lys  Val Gly Ala Gly Asn  Val Thr Ile Ala Lys  Gly Gly Lys
    1580                1585                1590

Val Lys  Ile Gly Glu Ile Gln  Gly Thr Gly Thr Asn  Thr Leu Thr
    1595                1600                1605

Leu Pro  Ala His Phe Asn Leu  Thr Gly Ser Ile Asn  Lys Thr Gly
    1610                1615                1620

Gly Gln  Ala Leu Lys Leu Asn  Phe Met Asn Gly Gly  Ser Val Ser
    1625                1630                1635

Gly Val  Val Gly Thr Ala Ala  Asn Ser Val Gly Asp  Ile Thr Thr
    1640                1645                1650

Ala Gly  Ala Thr Ser Phe Ala  Ser Ser Val Asn Ala  Lys Gly Thr
    1655                1660                1665

Ala Thr  Leu Gly Gly Thr Thr  Ser Phe Ala Asn Thr  Phe Thr Asn
    1670                1675                1680

Thr Gly  Ala Val Thr Leu Ala  Lys Gly Ser Ile Thr  Ser Phe Ala
    1685                1690                1695

Lys Asn  Val Thr Ala Thr Ser  Phe Val Ala Asn Ser  Ala Thr Ile
    1700                1705                1710

Asn Phe  Ser Asn Ser Leu Ala  Phe Asn Ser Asn Ile  Thr Gly Gly
    1715                1720                1725

Gly Thr  Thr Leu Thr Leu Gly  Ala Asn Gln Val Thr  Tyr Thr Gly
    1730                1735                1740

Thr Gly  Ser Phe Thr Asp Thr  Leu Thr Leu Asn Thr  Thr Phe Asp
    1745                1750                1755

Gly Ala  Ala Lys Ser Gly Gly  Asn Ile Leu Ile Lys  Ser Gly Ser
    1760                1765                1770

Thr Leu  Asp Leu Ser Gly Val  Ser Thr Leu Ala Leu  Val Val Thr
    1775                1780                1785

Ala Thr  Asn Phe Asp Met Asn  Asn Ile Ser Pro Asp  Thr Lys Tyr
    1790                1795                1800

Thr Val  Ile Ser Ala Glu Thr  Ala Gly Gly Leu Lys  Pro Thr Ser
    1805                1810                1815

Lys Glu  Asn Val Lys Ile Thr  Ile Asn Asn Asp Asn  Arg Phe Val
    1820                1825                1830

Asp Phe  Thr Phe Asp Ala Ser  Thr Leu Thr Leu Phe  Ala Glu Asp
    1835                1840                1845

Ile Ala  Ala Asp Val Ile Asp  Gly Asp Phe Ala Pro  Gly Gly Pro
    1850                1855                1860

Leu Ala  Asn Ile Pro Asn Ala  Ala Asn Ile Lys Lys  Ser Leu Glu
    1865                1870                1875

Leu Met  Glu Asp Ala Pro Asn  Gly Ser Asp Ala Arg  Gln Ala Phe
    1880                1885                1890

Asn Asn  Phe Gly Leu Met Thr  Pro Leu Gln Glu Ala  Asp Ala Thr
    1895                1900                1905
```

-continued

```
Thr His Leu Ile Gln Asp Val Val Lys Pro Ser Asp Thr Ile Ala
    1910                1915                1920

Ala Val Asn Asn Gln Val Val Ala Ser Asn Ile Ser Ser Asn Ile
    1925                1930                1935

Thr Ala Leu Asn Ala Arg Met Asp Lys Val Gln Ser Gly Asn Lys
    1940                1945                1950

Gly Pro Val Ser Ser Gly Asp Glu Asp Met Asp Ala Lys Phe Gly
    1955                1960                1965

Ala Trp Ile Ser Pro Phe Val Gly Asn Ala Thr Gln Lys Met Cys
    1970                1975                1980

Asn Ser Ile Ser Gly Tyr Lys Ser Asp Thr Thr Gly Gly Thr Ile
    1985                1990                1995

Gly Phe Asp Gly Phe Val Ser Asp Asp Leu Ala Leu Gly Leu Ala
    2000                2005                2010

Tyr Thr Arg Ala Asp Thr Asp Ile Lys Leu Lys Asn Asn Lys Thr
    2015                2020                2025

Gly Asp Lys Asn Lys Val Glu Ser Asn Ile Tyr Ser Leu Tyr Gly
    2030                2035                2040

Leu Tyr Asn Val Pro Tyr Glu Asn Leu Phe Val Glu Ala Ile Ala
    2045                2050                2055

Ser Tyr Ser Asp Asn Lys Ile Arg Ser Lys Ser Arg Arg Val Ile
    2060                2065                2070

Ala Thr Thr Leu Glu Thr Val Gly Tyr Gln Thr Ala Asn Gly Lys
    2075                2080                2085

Tyr Lys Ser Glu Ser Tyr Thr Gly Gln Leu Met Ala Gly Tyr Thr
    2090                2095                2100

Tyr Met Met Pro Glu Asn Ile Asn Leu Thr Pro Leu Ala Gly Leu
    2105                2110                2115

Arg Tyr Ser Thr Ile Lys Asp Lys Gly Tyr Lys Glu Thr Gly Thr
    2120                2125                2130

Thr Tyr Gln Asn Leu Thr Val Lys Gly Lys Asn Tyr Asn Thr Phe
    2135                2140                2145

Asp Gly Leu Leu Gly Ala Lys Val Ser Ser Asn Ile Asn Val Asn
    2150                2155                2160

Glu Ile Val Leu Thr Pro Glu Leu Tyr Ala Met Val Asp Tyr Ala
    2165                2170                2175

Phe Lys Asn Lys Val Ser Ala Ile Asp Ala Arg Leu Gln Gly Met
    2180                2185                2190

Thr Ala Pro Leu Pro Thr Asn Ser Phe Lys Gln Ser Lys Thr Ser
    2195                2200                2205

Phe Asp Val Gly Val Gly Val Thr Ala Lys His Lys Met Met Glu
    2210                2215                2220

Tyr Arg Ile Asn Tyr Asp Thr Asn Ile Gly Ser Lys Tyr Phe Ala
    2225                2230                2235

Gln Gln Gly Ser Val Lys Val Arg Val Asn Phe
    2240                2245
```

```
<210> SEQ ID NO 2
<211> LENGTH: 6750
<212> TYPE: DNA
<213> ORGANISM: Rickettsia rickettsii
<220> FEATURE:
<221> NAME/KEY: misc_feature
<223> OTHER INFORMATION: OmpA nucleotide sequence

<400> SEQUENCE: 2
```

-continued

```
atggcgaata tttctccaaa attatttaaa aaagcaatac aacaaggtct taaagccgct     60
ttattcacca cctcaaccgc agcgataatg ctgagtagta gcggggcact cggtgttgct    120
acaggtgtta ttgctactaa taataatgca gcatttagta ataatgttgg caataataat    180
tggaatgaga taacggctgc aggggtagct aatggtactc ctgctggcgg tcctcaaaac    240
aattgggcat ttacttacgg tggtgattat actgtcactg cagatgcagc cgatcgtatt    300
attaaggcta taaatgttgc gggtactact cccgtaggtc taaatattac tcaaaatact    360
gtcgttggtt cgattataac gaaaggtaac ttgttgcctg ttactcttaa tgccggcaaa    420
agcttaactt taaatggtaa taatgctgtt gctgcaaatc atggttttga tgcgcctgcc    480
gataattata caggtttagg aaatatagct ttagggggag cgaatgctgc actaattata    540
caatctgcag ctccgtcaaa gataacactt gcaggaaata tagatggagg aggtataata    600
actgtcaaga cagatgctgc cattaacgga acaataggta atacaaatgc attagcaaca    660
gtgaatgtag gagcaggtac agccacgtta gggggagcgg ttattaaagc tactacgact    720
aaattaacga atgctgcgtc ggtattaacc cttacaaatg caaatgcagt attaacaggt    780
gcgattgata acaccacagg cggtgataat gtaggtgtct taaatttaaa tggtgcatta    840
agtcaagtaa ctggggatat aggtaataca aattcattag ccacgataag tgtaggagca    900
ggtacagcca cgttaggggg agcggttatt aaagctacta cgactaagtt gacagatgct    960
gcgtcagcag tgaaatttac gaatcctgta gtggtgactg gagcgataga taataccggt   1020
aatgcaaata atggtatagt aacgtttacc ggtaatagta cagtaactgg gaatgtaggt   1080
aatacaaatg cattagcaac agtgaatgta ggagcaggtt tgctacaagt acaaggtgga   1140
gtggtaaaag caaatacaat aaacttaacg gataatgcgt cagcagtgac atttacgaat   1200
cctgtagtgg tgaccggagc gatagataat accggtaatg caaataatgg tatagtaacg   1260
tttaccggta atagtacagt aactggggat ataggtaata caaatgcatt agcaacagtg   1320
aatgtaggag caggtacagc cacgctaggg ggagcggtta ttaaagctac tacgactaaa   1380
ttaacgaatg ctgcgtcggt attaaccctt acaaatgcaa atgcagtatt aacaggtgcg   1440
attgataaca ccacaggcgg tgataatgta ggtgtcttaa atttaaatgg tgcattaagt   1500
caagtaactg ggaatatagg taatacaaat tcattagcca cgataagtgt aggagcaggt   1560
acagccacgt tagggggagc ggttattaaa gctactacga ctaagttgac agatgctgcg   1620
tcagcagtga aatttacgaa tcctgtagtg gtgactggag cgatagataa taccggtaat   1680
gcaaataatg gtatagtaac gtttaccggt aatagtacag taactgggga tataggtaat   1740
acaaattcat tagccacgat aagtgtagga gcaggtacag ccacgttagg gggagcagtt   1800
attaaagcta ctacgactaa attaacgaat gctgcgtcgg tattaaccct tacaaatgca   1860
aatgcagtat taacaggtgc gattgataac accacaggcg gtgataatgt aggtgtctta   1920
aatttaaatg gtgcattaag tcaagtaact ggggatatag gtaatacaaa ttcattagcc   1980
acgataagtg taggagcagg tacagccacg ttagggggag cggttattaa agctactacg   2040
actaaaataa cgaatgctgt gtcagcagtg aaatttacga atcctgtagt ggtgaccgga   2100
gcgatagata gtaccggtaa tgccaataat ggtatagtaa cgtttaccgg taatagtaca   2160
gtaactgggg atataggtaa tacaaatgca ttagcaacag tgaatgtagg agcaggtaca   2220
gccacgctag gggagcggt tattaaagct actacgacta agttaacgaa tgctgcgtcg   2280
gtattaaccc ttacaaatgc aaatgcagta ttaacaggtg cgattgataa caccacaggc   2340
ggtgataatg taggtgtctt aaatttaaat ggtgcgttaa gtcaagtaac tggggatata   2400
```

-continued

```
ggtaatacaa attcattagc cacgataagt gtaggagcag gtacagccac gttaggggga   2460
gcggttatta aagctactac gactaaatta acgaatgctg cgtcggtatt aacccttaca   2520
aatgcaaatg cagtattaac aggtgcggtt gataacacca caggcggtga taatgtaggt   2580
gtcttaaatt taaatggtgc gttaagtcaa gtaactgggg atataggtaa tacaaattca   2640
ttagccacga taagtgtagg agcaggtaca gccacgttag gggagcggt tattaaagct    2700
actacgacta aattaacgaa tgctgcgtcg gtattaaccc ttacaaatgc aaatgcagta   2760
ttaacaggtg cgattgataa caccacaggc ggtgataatg taggtgtctt aaatttaaat   2820
ggtgcgttaa gtcaagtaac tggggatata ggtaatacaa attcattagc cacgataagt   2880
gtaggagcag gtacagccac gttaggggga gcggttatta aagctactac gactaagttg   2940
acagatgctg cgtcagcagt gaaatttacg aatcctgtag tggtgaccgg agcgatagat   3000
aataccggta atgcaaataa tggtatagta acgtttaccg gtaatagtac agtaactggg   3060
aatgtaggta atacaaatgc attagcaaca gtgaatgtag gagcaggttt gctacaagta   3120
caaggtggag tggtaaaagc aaatacaata aacttaacgg ataatgcgtc agcagtgaca   3180
tttacgaatc ctgtagtggt gaccggagcg atagataata ccggtaatgc aaataatggt   3240
atagtaacgt ttaccggtaa tagtacagta actgggaatg taggtaatac aaatgcatta   3300
gcaacagtga atgtaggagc aggtttgcta caagtacaag gtggagtggt aaaagcaaat   3360
acaataaact taacggataa tgcgtcagca gtgacattta cgaatcctgt agtggtgacc   3420
ggagcgatag ataataccgg taatgcaaat aatggtatag taacgtttac cggtaatagt   3480
acagtaactg ggatatagg taatacaaat gcattagcaa cagtgaatgt aggagcagga    3540
ataacattac aagctggagg aagcctagct gcgaataata tagattttgg agccaggagt   3600
actttagagt ttaacggacc tcttgatggt ggtggtaaag caatccctta ttattttaaa   3660
ggagctatag caaacggcaa taatgctata ttaaatgtta atacaaagtt acttacggca   3720
tctcatttaa ctataggaac agttgcagaa atcaatattg gagctggtaa tctttttaca   3780
attgatgcaa gtgttggtga tgttactata ttaaatgctc aaaatattaa ttttagagct   3840
cgagattctg ttttagtact ttctaactta accggagtcg gagtaaataa tatattatta   3900
gcagctgatt tagtagctcc cggtgctgat gaaggtacgg tagtctttaa tggtggggtt   3960
aatggcctga atgttgggag taatgtagca ggtaccgcta gaaatatcgg tgatggaggc   4020
ggtaataaat ttaacacttt acttatttat aatgctgtta caataactga cgatgtaaat   4080
ttagaaggta tacagaacgt gcttattaac aagaatgcag atttactag tagtacagca    4140
tttaatgctg gtgctataca aataaacgat gctacttata cgattgatgc aaataatggt   4200
aatttaaata taccggcagg aaatattcaa tttgcacatg cggatgctca attagtatta   4260
caaaatagtt caggaaacga ccgtacgata acactaggtg cgaatataga ccctgataat   4320
gacgatgagg gtatagtaat attaaattct gtaactgcag gaaaaaaatt aacgatagcc   4380
ggaggcaaga cgtttggtgg agctcataag ttacaaacta tattgttcaa aggagcggga   4440
gattgtagca cggcaggtac cacttttaat acaacaaata tagtacttga tattacaggt   4500
caattagaac ttggagctac tacggcaaat gtagttttat ttaatgatgc tgttcaatta   4560
actcaaaccg gtaatattgg cggtttctta gattttaatg caaaaaacgg tatggtaaca   4620
ttaaataaca atgtaaatgt tgcgggagca gtccaaaata ccggcggtac taataacggt   4680
acgttaatag ttttaggtgc aagtaatctt aatagagtaa acgggattgc tatgttaaaa   4740
gtaggtgcag gaaatgtaac tattgccaaa ggcggtaaag ttaaaatcgg cgaaatccaa   4800
```

-continued

```
ggtacaggca caaatacttt aacattacct gcacacttta acttaacagg cagcataaat   4860

aaaaccggtg gtcaggctct gaagctaaac ttcatgaatg gcggtagtgt tagcggtgtt   4920

gtagggactg cggctaattc ggttggtgat atcacaacgg caggtgctac aagttttgca   4980

agcagtgtta acgcaaaagg tacggcgaca cttggcggta ctacaagttt tgccaataca   5040

ttcactaata caggtgcggt tactttagcc aaaggttcta tcactagttt tgctaaaaat   5100

gtaacggcta ccagctttgt agctaacagt gctactatta atttcagcaa tagcctagcc   5160

tttaatagta atataacagg tggcggtact acacttactt taggtgcaaa tcaagtaaca   5220

tatactggca ccggtagctt taccgatacg ctaaccttaa atactacttt tgacggagca   5280

gctaagtcag gtggtaatat cttaattaaa tcaggtagta ctcttgattt atcaggggtt   5340

tcaactttag cacttgttgt tactgctact aatttcgaca tgaataatat aagcccagat   5400

acaaaatata cggtaatatc tgcagaaaca gcaggtggtt taaagcctac ttctaaagag   5460

aatgttaaaa taactattaa taatgacaac cgttttgttg actttacttt tgatgcatcg   5520

actttaacgt tatttgcaga agatatagct gcagatgtta tagatggaga ttttgcaccg   5580

ggtggaccgc ttgcaaatat cccaaatgct gcaaatataa agaaatcgct tgagttaatg   5640

gaggatgctc ccaatggttc agatgcacgt caagctttca ataactttgg tctaatgaca   5700

ccgctacagg aagcagatgc tacaactcat ctcattcaag atgttgtaaa acctagcgac   5760

actatagctg ccgttaataa tcaagttgta gcgagtaata tatcaagtaa tataactgct   5820

ctaaatgcta gaatggataa agtacaatca gggaataaag gtcctgtttc ttctggtgat   5880

gaagatatgg atgctaagtt tggtgcgtgg ataagcccgt ttgtcggtaa tgcaacgcag   5940

aagatgtgta acagtataag tggttataag tctgatacaa ctggtggcac tataggtttt   6000

gacggcttcg ttagcgatga tctagcactc ggacttgcat atacaagagc cgatactgac   6060

attaagctaa aaaataataa aacgggcgat aagaataagg tagagagcaa catctattct   6120

ttatacggtt tatataatgt accttatgaa aatctcttcg ttgaagctat agcatcttac   6180

tcagataata agataagaag caaatcaaga cgtgttattg caacgacact agagactgtc   6240

ggttatcaaa ctgcaaacgg taagtataaa tccgaaagct atacaggtca gttaatggct   6300

ggttatacct atatgatgcc tgagaacatt aacttaacac cgctagctgg gcttagatat   6360

tcgactatca aagataaggg ctataaggaa accggtacta cttaccaaaa tcttaccgtt   6420

aaaggcaaga actataatac tttcgacggt ttactcggtg ctaaagtatc aagtaatatc   6480

aatgtcaatg aaatagtgct aacacctgag ctttacgcaa tggtcgatta tgcattcaag   6540

aataaagttt cggcgattga tgcaaggtta caaggtatga ctgctcctct tccaaccaac   6600

agctttaagc aaagcaaaac aagttttgat gtcggtgtcg gtgttactgc taagcataaa   6660

atgatggaat acaggattaa ctacgatacc aatatcggaa gtaagtattt cgctcagcaa   6720

ggtagtgtaa aagttcgtgt taatttttaa                                     6750
```

```
<210> SEQ ID NO 3
<211> LENGTH: 242
<212> TYPE: PRT
<213> ORGANISM: Rickettsia rickettsii
<220> FEATURE:
<221> NAME/KEY: MISC_FEATURE
<223> OTHER INFORMATION: OmpA fragment X polypeptide

<400> SEQUENCE: 3

Arg Asp Ser Val Leu Val Leu Ser Asn Leu Thr Gly Val Gly Val Asn
1               5                   10                  15
```

-continued

```
Asn Ile Leu Leu Ala Ala Asp Leu Val Ala Pro Gly Ala Asp Glu Gly
            20                  25                  30

Thr Val Val Phe Asn Gly Gly Val Asn Gly Leu Asn Val Gly Ser Asn
        35                  40                  45

Val Ala Gly Thr Ala Arg Asn Ile Gly Asp Gly Gly Gly Asn Lys Phe
    50                  55                  60

Asn Thr Leu Leu Ile Tyr Asn Ala Val Thr Ile Thr Asp Asp Val Asn
65                  70                  75                  80

Leu Glu Gly Ile Gln Asn Val Leu Ile Asn Lys Asn Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Val Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
            180                 185                 190

Thr Ile Leu Phe Lys Gly Ala Gly Asp Cys Ser Thr Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Asn Val Val Leu Phe Asn Asp Ala Val Gln Leu
225                 230                 235                 240

Thr Gln
```

<210> SEQ ID NO 4
<211> LENGTH: 726
<212> TYPE: DNA
<213> ORGANISM: Rickettsia rickettsii
<220> FEATURE:
<221> NAME/KEY: misc_feature
<223> OTHER INFORMATION: OmpA Fragment X Nucleotide

<400> SEQUENCE: 4

```
cgagattctg ttttagtact ttctaactta accggagtcg gagtaaataa tatattatta     60

gcagctgatt tagtagctcc cggtgctgat gaaggtacgg tagtctttaa tggtggggtt    120

aatggcctga atgttgggag taatgtagca ggtaccgcta gaaatatcgg tgatggaggc    180

ggtaataaat ttaacacttt acttatttat aatgctgtta caataactga cgatgtaaat    240

ttagaaggta tacagaacgt gcttattaac aagaatgcag attttactag tagtacagca    300

tttaatgctg gtgctataca aataaacgat gctacttata cgattgatgc aaataatggt    360

aatttaaata taccggcagg aaatattcaa tttgcacatg cggatgctca attagtatta    420

caaaatagtt caggaaacga ccgtacgata acactaggtg cgaatataga ccctgataat    480

gacgatgagg gtatagtaat attaaattct gtaactgcag gaaaaaaatt aacgatagcc    540

ggaggcaaga cgtttggtgg agctcataag ttacaaacta tattgttcaa aggagcggga    600

gattgtagca cggcaggtac cacttttaat acaacaaata tagtacttga tattacaggt    660

caattagaac ttggagctac tacggcaaat gtagttttat ttaatgatgc tgttcaatta    720

actcaa                                                                726
```

-continued

<210> SEQ ID NO 5
<211> LENGTH: 250
<212> TYPE: PRT
<213> ORGANISM: Rickettsia rickettsii
<220> FEATURE:
<221> NAME/KEY: MISC_FEATURE
<223> OTHER INFORMATION: OmpA Fragment Y polypeptide

<400> SEQUENCE: 5

```
Val Thr Ala Thr Ser Phe Val Ala Asn Ser Ala Thr Ile Asn Phe Ser
1               5                   10                  15

Asn Ser Leu Ala Phe Asn Ser Asn Ile Thr Gly Gly Gly Thr Thr Leu
            20                  25                  30

Thr Leu Gly Ala Asn Gln Val Thr Tyr Thr Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Thr Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110

Gly Leu Lys Pro Thr Ser Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Asp Val Ile Asp Gly Asp Phe Ala Pro
145                 150                 155                 160

Gly Gly Pro Leu Ala Asn Ile Pro Asn Ala Ala Asn Ile Lys Lys Ser
                165                 170                 175

Leu Glu Leu Met Glu Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Ile Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Ser
                245                 250
```

<210> SEQ ID NO 6
<211> LENGTH: 750
<212> TYPE: DNA
<213> ORGANISM: Rickettsia rickettsii
<220> FEATURE:
<221> NAME/KEY: misc_feature
<223> OTHER INFORMATION: OmpA Fragment Y Nucleotide

<400> SEQUENCE: 6

```
gtaacggcta ccagctttgt agctaacagt gctactatta atttcagcaa tagcctagcc      60

tttaatagta atataacagg tggcggtact acacttactt taggtgcaaa tcaagtaaca     120

tatactggca ccggtagctt taccgatacg ctaaccttaa atactacttt tgacggagca     180

gctaagtcag gtggtaatat cttaattaaa tcaggtagta ctcttgattt atcaggggtt     240

tcaactttag cacttgttgt tactgctact aatttcgaca tgaataatat aagcccagat     300
```

acaaaatata cggtaatatc tgcagaaaca gcaggtggtt taaagcctac ttctaaagag 360
aatgttaaaa taactattaa taatgacaac cgttttgttg actttacttt tgatgcatcg 420
actttaacgt tatttgcaga agatatagct gcagatgtta tagatggaga ttttgcaccg 480
ggtggaccgc ttgcaaatat cccaaatgct gcaaatataa agaaatcgct tgagttaatg 540
gaggatgctc ccaatggttc agatgcacgt caagctttca ataactttgg tctaatgaca 600
ccgctacagg aagcagatgc tacaactcat ctcattcaag atgttgtaaa acctagcgac 660
actatagctg ccgttaataa tcaagttgta gcgagtaata tatcaagtaa tataactgct 720
ctaaatgcta gaatggataa agtacaatca 750

<210> SEQ ID NO 7
<211> LENGTH: 36
<212> TYPE: DNA
<213> ORGANISM: Rickettsia rickettsii

<400> SEQUENCE: 7
ggtggtcata tgcgagattc tgttttagta ctttct 36

<210> SEQ ID NO 8
<211> LENGTH: 37
<212> TYPE: DNA
<213> ORGANISM: Rickettsia rickettsii

<400> SEQUENCE: 8
ggtggtctcg agttgagtta attgaacagc atcatta 37

<210> SEQ ID NO 9
<211> LENGTH: 34
<212> TYPE: DNA
<213> ORGANISM: Rickettsia rickettsii

<400> SEQUENCE: 9
ggtggtcata tggtaacggc taccagcttt gtag 34

<210> SEQ ID NO 10
<211> LENGTH: 36
<212> TYPE: DNA
<213> ORGANISM: Rickettsia rickettsii

<400> SEQUENCE: 10
ggtggtctcg agtgattgta ctttatccat tctagc 36

<210> SEQ ID NO 11
<211> LENGTH: 670
<212> TYPE: PRT
<213> ORGANISM: Rickettsia rickettsii
<220> FEATURE:
<221> NAME/KEY: MISC_FEATURE
<223> OTHER INFORMATION: OmAp_Z polypeptide

<400> SEQUENCE: 11

Arg Asp Ser Val Leu Val Leu Ser Asn Leu Thr Gly Val Gly Val Asn
1 5 10 15

Asn Ile Leu Leu Ala Ala Asp Leu Val Ala Pro Gly Ala Asp Glu Gly
20 25 30

Thr Val Val Phe Asn Gly Gly Val Asn Gly Leu Asn Val Gly Ser Asn
35 40 45

Val Ala Gly Thr Ala Arg Asn Ile Gly Asp Gly Gly Gly Asn Lys Phe
50 55 60

-continued

```
Asn Thr Leu Leu Ile Tyr Asn Ala Val Thr Ile Thr Asp Asp Val Asn
65                  70                  75                  80

Leu Glu Gly Ile Gln Asn Val Leu Ile Asn Lys Asn Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Val Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
            180                 185                 190

Thr Ile Leu Phe Lys Gly Ala Gly Asp Cys Ser Thr Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Asn Val Val Leu Phe Asn Asp Ala Val Gln Leu
225                 230                 235                 240

Thr Gln Thr Gly Asn Ile Gly Gly Phe Leu Asp Phe Asn Ala Lys Asn
                245                 250                 255

Gly Met Val Thr Leu Asn Asn Asn Val Asn Val Ala Gly Ala Val Gln
            260                 265                 270

Asn Thr Gly Gly Thr Asn Asn Gly Thr Leu Ile Val Leu Gly Ala Ser
        275                 280                 285

Asn Leu Asn Arg Val Asn Gly Ile Ala Met Leu Lys Val Gly Ala Gly
    290                 295                 300

Asn Val Thr Ile Ala Lys Gly Gly Lys Val Lys Ile Gly Glu Ile Gln
305                 310                 315                 320

Gly Thr Gly Thr Asn Thr Leu Thr Leu Pro Ala His Phe Asn Leu Thr
                325                 330                 335

Gly Ser Ile Asn Lys Thr Gly Gly Gln Ala Leu Lys Leu Asn Phe Met
            340                 345                 350

Asn Gly Gly Ser Val Ser Gly Val Val Gly Thr Ala Ala Asn Ser Val
        355                 360                 365

Gly Asp Ile Thr Thr Ala Gly Ala Thr Ser Phe Ala Ser Ser Val Asn
    370                 375                 380

Ala Lys Gly Thr Ala Thr Leu Gly Gly Thr Thr Ser Phe Ala Asn Thr
385                 390                 395                 400

Phe Thr Asn Thr Gly Ala Val Thr Leu Ala Lys Gly Ser Ile Thr Ser
                405                 410                 415

Phe Ala Lys Asn Val Thr Ala Thr Ser Phe Val Ala Asn Ser Ala Thr
            420                 425                 430

Ile Asn Phe Ser Asn Ser Leu Ala Phe Asn Ser Asn Ile Thr Gly Gly
        435                 440                 445

Gly Thr Thr Leu Thr Leu Gly Ala Asn Gln Val Thr Tyr Thr Gly Thr
    450                 455                 460

Gly Ser Phe Thr Asp Thr Leu Thr Leu Asn Thr Thr Phe Asp Gly Ala
465                 470                 475                 480

Ala Lys Ser Gly Gly Asn Ile Leu Ile Lys Ser Gly Ser Thr Leu Asp
                485                 490                 495
```

-continued

```
Leu Ser Gly Val Ser Thr Leu Ala Leu Val Val Thr Ala Thr Asn Phe
            500                 505                 510

Asp Met Asn Asn Ile Ser Pro Asp Thr Lys Tyr Thr Val Ile Ser Ala
        515                 520                 525

Glu Thr Ala Gly Gly Leu Lys Pro Thr Ser Lys Glu Asn Val Lys Ile
    530                 535                 540

Thr Ile Asn Asn Asp Asn Arg Phe Val Asp Phe Thr Phe Asp Ala Ser
545                 550                 555                 560

Thr Leu Thr Leu Phe Ala Glu Asp Ile Ala Ala Asp Val Ile Asp Gly
                565                 570                 575

Asp Phe Ala Pro Gly Gly Pro Leu Ala Asn Ile Pro Asn Ala Ala Asn
            580                 585                 590

Ile Lys Lys Ser Leu Glu Leu Met Glu Asp Ala Pro Asn Gly Ser Asp
        595                 600                 605

Ala Arg Gln Ala Phe Asn Asn Phe Gly Leu Met Thr Pro Leu Gln Glu
    610                 615                 620

Ala Asp Ala Thr Thr His Leu Ile Gln Asp Val Val Lys Pro Ser Asp
625                 630                 635                 640

Thr Ile Ala Ala Val Asn Asn Gln Val Val Ala Ser Asn Ile Ser Ser
                645                 650                 655

Asn Ile Thr Ala Leu Asn Ala Arg Met Asp Lys Val Gln Ser
            660                 665                 670
```

```
<210> SEQ ID NO 12
<211> LENGTH: 2010
<212> TYPE: DNA
<213> ORGANISM: Rickettsia rickettsii
<220> FEATURE:
<221> NAME/KEY: misc_feature
<223> OTHER INFORMATION: OmpA_Z nucleotide

<400> SEQUENCE: 12

cgagattctg ttttagtact ttctaactta accggagtcg gagtaaataa tatattatta     60

gcagctgatt tagtagctcc cggtgctgat gaaggtacgg tagtctttaa tggtggggtt    120

aatggcctga atgttgggag taatgtagca ggtaccgcta gaaatatcgg tgatggaggc    180

ggtaataaat ttaacacttt acttatttat aatgctgtta caataactga cgatgtaaat    240

ttagaaggta tacagaacgt gcttattaac aagaatgcag attttactag tagtacagca    300

tttaatgctg gtgctataca aataaacgat gctacttata cgattgatgc aaataatggt    360

aatttaaata taccggcagg aaatattcaa tttgcacatg cggatgctca attagtatta    420

caaaatagtt caggaaacga ccgtacgata acactaggtg cgaatataga ccctgataat    480

gacgatgagg gtatagtaat attaaattct gtaactgcag gaaaaaaatt aacgatagcc    540

ggaggcaaga cgtttggtgg agctcataag ttacaaacta tattgttcaa aggagcggga    600

gattgtagca cggcaggtac cacttttaat acaacaaata tagtacttga tattacaggt    660

caattagaac ttggagctac tacggcaaat gtagttttat ttaatgatgc tgttcaatta    720

actcaaaccg gtaatattgg cggtttctta gattttaatg caaaaaacgg tatggtaaca    780

ttaaataaca atgtaaatgt tgcgggagca gtccaaaata ccggcggtac taataacggt    840

acgttaatag ttttaggtgc aagtaatctt aatagagtaa acgggattgc tatgttaaaa    900

gtaggtgcag gaaatgtaac tattgccaaa ggcggtaaag ttaaaatcgg cgaaatccaa    960

ggtacaggca caaatacttt aacattacct gcacacttta acttaacagg cagcataaat   1020

aaaaccggtg gtcaggctct gaagctaaac ttcatgaatg gcggtagtgt tagcggtgtt   1080
```

-continued

```
gtagggactg cggctaattc ggttggtgat atcacaacgg caggtgctac aagttttgca   1140

agcagtgtta acgcaaaagg tacggcgaca cttggcggta ctacaagttt tgccaataca   1200

ttcactaata caggtgcggt tactttagcc aaaggttcta tcactagttt tgctaaaaat   1260

gtaacggcta ccagctttgt agctaacagt gctactatta atttcagcaa tagcctagcc   1320

tttaatagta atataacagg tggcggtact acacttactt taggtgcaaa tcaagtaaca   1380

tatactggca ccggtagctt taccgatacg ctaaccttaa atactacttt tgacggagca   1440

gctaagtcag gtggtaatat cttaattaaa tcaggtagta ctcttgattt atcaggggtt   1500

tcaactttag cacttgttgt tactgctact aatttcgaca tgaataatat aagcccagat   1560

acaaaatata cggtaatatc tgcagaaaca gcaggtggtt taaagcctac ttctaaagag   1620

aatgttaaaa taactattaa taatgacaac cgttttgttg actttacttt tgatgcatcg   1680

actttaacgt tatttgcaga agatatagct gcagatgtta tagatggaga ttttgcaccg   1740

ggtggaccgc ttgcaaatat cccaaatgct gcaaatataa agaaatcgct tgagttaatg   1800

gaggatgctc ccaatggttc agatgcacgt caagctttca ataactttgg tctaatgaca   1860

ccgctacagg aagcagatgc tacaactcat ctcattcaag atgttgtaaa acctagcgac   1920

actatagctg ccgttaataa tcaagttgta gcgagtaata tatcaagtaa tataactgct   1980

ctaaatgcta gaatggataa agtacaatca                                     2010


<210> SEQ ID NO 13
<211> LENGTH: 242
<212> TYPE: PRT
<213> ORGANISM: Rickettsia slovaca

<400> SEQUENCE: 13

Leu Asp Ser Ala Leu Val Leu Ser Asn Leu Thr Gly Val Gly Val Asn
1               5                   10                  15

Asn Ile Leu Leu Ala Ala Asp Leu Val Ala Pro Gly Ala Asp Glu Gly
            20                  25                  30

Thr Val Val Phe Asn Gly Gly Val Asn Gly Leu Asn Ile Gly Ser Asn
        35                  40                  45

Val Ala Gly Thr Ala Arg Asn Ile Gly Asp Gly Gly Gly Asn Lys Phe
    50                  55                  60

Asn Thr Leu Leu Ile Tyr Asn Ala Val Thr Ile Thr Asp Asp Val Asn
65                  70                  75                  80

Leu Glu Gly Ile Gln Asn Val Leu Ile Asn Asn Asn Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Ile Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
            180                 185                 190

Thr Ile Val Phe Lys Gly Ala Gly Asp Cys Gly Ala Ala Gly Thr Thr
        195                 200                 205
```

```
Phe Asn Thr Thr Asn Ile Glu Leu Asn Ile Thr Gly Gln Leu Glu Leu
    210                 215                 220

Gly Ala Thr Thr Ala Asn Val Val Leu Phe Asn Asp Ala Val Gln Leu
225                 230                 235                 240

Thr Gln


<210> SEQ ID NO 14
<211> LENGTH: 242
<212> TYPE: PRT
<213> ORGANISM: Rickettsia honei

<400> SEQUENCE: 14

Leu Asp Ser Ala Leu Val Leu Ser Asn Leu Thr Gly Val Gly Val Asn
1               5                   10                  15

Asn Ile Leu Leu Ala Ala Asp Leu Val Ala Pro Gly Ala Asp Glu Gly
            20                  25                  30

Thr Val Val Phe Asn Gly Gly Val Asn Gly Leu Asn Ile Gly Ser Asn
        35                  40                  45

Val Ala Gly Thr Ala Arg Asn Ile Gly Asp Gly Gly Gly Asn Lys Phe
    50                  55                  60

Asn Thr Leu Ser Ile Tyr Asn Ala Val Thr Ile Thr Asp Asp Val Asn
65                  70                  75                  80

Leu Glu Gly Ile Gln Asn Val Leu Ile Asn Asp Asn Ala Asp Phe Thr
                85                  90                  95

Ser Ser Thr Ala Phe Asn Ala Gly Thr Ile Gln Ile Lys Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Ile Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Met Phe Gly Gly Ala His Lys Leu Gln
            180                 185                 190

Thr Ile Val Phe Lys Gly Ala Gly Asn Cys Gly Ala Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Ser Val Val Leu Phe Asn Asp Ala Val Gln Leu
225                 230                 235                 240

Thr Gln


<210> SEQ ID NO 15
<211> LENGTH: 242
<212> TYPE: PRT
<213> ORGANISM: Rickettsia rickettsii

<400> SEQUENCE: 15

Arg Asp Ser Val Leu Val Leu Ser Asn Leu Thr Gly Val Gly Val Asn
1               5                   10                  15

Asn Ile Leu Leu Ala Ala Asp Leu Val Ala Pro Gly Ala Asp Glu Gly
            20                  25                  30

Thr Val Val Phe Asn Gly Gly Val Asn Gly Leu Asn Val Gly Ser Asn
        35                  40                  45
```

```
Val Ala Gly Thr Ala Arg Asn Ile Gly Asp Gly Gly Gly Asn Lys Phe
    50                  55                  60

Asn Thr Leu Leu Ile Tyr Asn Ala Val Thr Ile Thr Asp Asp Val Asn
65                  70                  75                  80

Leu Glu Gly Ile Gln Asn Val Leu Ile Asn Lys Asn Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Val Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
            180                 185                 190

Thr Ile Leu Phe Lys Gly Ala Gly Asp Cys Ser Thr Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Asn Val Val Leu Phe Asn Asp Ala Val Gln Leu
225                 230                 235                 240

Thr Gln


<210> SEQ ID NO 16
<211> LENGTH: 242
<212> TYPE: PRT
<213> ORGANISM: Rickettsia peacockii

<400> SEQUENCE: 16

Leu Asp Ser Val Leu Val Leu Ser Asn Leu Thr Gly Val Gly Val Asn
1               5                   10                  15

Asn Ile Leu Leu Ala Ala Asp Leu Val Ala Pro Gly Ala Asp Glu Gly
            20                  25                  30

Thr Ile Val Phe Asn Gly Gly Val Asn Gly Leu Asn Ile Gly Ser Asn
        35                  40                  45

Val Ala Gly Thr Ala Arg Asn Ile Gly Asp Gly Gly Gly Asn Lys Phe
    50                  55                  60

Asn Thr Leu Leu Ile Tyr Asn Ala Val Thr Ile Thr Asp Asp Val Asn
65                  70                  75                  80

Leu Glu Gly Ile Gln Asn Val Leu Ile Asn Asn Asn Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Val Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
```

```
            180                 185                 190

Thr Ile Leu Phe Lys Gly Ala Gly Asp Cys Ser Ala Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Asn Val Val Leu Phe Asn Asp Ala Val Gln Leu
225                 230                 235                 240

Thr Gln


<210> SEQ ID NO 17
<211> LENGTH: 242
<212> TYPE: PRT
<213> ORGANISM: Rickettsia parkeri

<400> SEQUENCE: 17

Leu Asp Ser Gly Leu Val Leu Ser Asn Leu Thr Gly Val Gly Val Asn
1               5                   10                  15

Asn Ile Leu Leu Ala Ala Asp Leu Val Ala Pro Gly Ala Asp Glu Gly
            20                  25                  30

Thr Val Ile Phe Asn Gly Gly Val Asn Gly Leu Asn Ile Gly Ser Asn
        35                  40                  45

Val Ala Gly Thr Ala Arg Asn Ile Gly Asp Gly Gly Gly Asn Lys Phe
    50                  55                  60

Asn Thr Leu Leu Ile Asp Asn Ala Val Thr Ile Thr Asp Asp Val Asn
65                  70                  75                  80

Leu Glu Gly Ile Gln Asn Val Leu Ile Asn Asn Lys Ala Asp Phe Thr
                85                  90                  95

Ser Ser Thr Ala Phe Asn Ala Gly Ala Ile Gln Ile Asn Asp Ala Thr
            100                 105                 110

Tyr Thr Ile Asp Ala Asn Asn Gly Asn Leu Asn Ile Pro Ala Gly Asn
        115                 120                 125

Ile Gln Phe Ala His Ala Asp Ala Gln Leu Ile Leu Gln Asn Ser Ser
    130                 135                 140

Gly Asn Asp Arg Thr Ile Thr Leu Gly Ala Asn Ile Asp Pro Asp Asn
145                 150                 155                 160

Asp Asp Glu Gly Ile Val Ile Leu Asn Ser Val Thr Ala Gly Lys Lys
                165                 170                 175

Leu Thr Ile Ala Gly Gly Lys Thr Phe Gly Gly Ala His Lys Leu Gln
            180                 185                 190

Thr Ile Val Phe Lys Gly Ala Gly Asp Cys Gly Thr Ala Gly Thr Thr
        195                 200                 205

Phe Asn Thr Thr Asn Ile Val Leu Asp Ile Thr Gly Gln Leu Glu Leu
    210                 215                 220

Gly Ala Thr Thr Ala Asn Val Val Leu Phe Lys Asp Ala Val Gln Leu
225                 230                 235                 240

Thr Gln


<210> SEQ ID NO 18
<211> LENGTH: 250
<212> TYPE: PRT
<213> ORGANISM: Rickettsia honei

<400> SEQUENCE: 18

Val Thr Ala Thr Ser Phe Val Ala Asn Ser Ala Thr Ile Asn Phe Gly
1               5                   10                  15

Asn Ser Leu Ala Phe Asn Ser Asn Ile Thr Gly Ser Gly Thr Thr Leu
```

```
            20                  25                  30

Thr Leu Gly Ala Asn Gln Val Thr Tyr Thr Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Thr Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110

Gly Leu Lys Pro Thr Pro Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Asp Val Ile Asp Glu Asp Phe Ala Pro
145                 150                 155                 160

Gly Gly Pro Leu Ala Asn Ile Pro Asn Ala Ala Asn Ile Lys Lys Ser
                165                 170                 175

Leu Glu Leu Met Glu Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Met Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Ala
                245                 250


<210> SEQ ID NO 19
<211> LENGTH: 250
<212> TYPE: PRT
<213> ORGANISM: Rickettsia conorii

<400> SEQUENCE: 19

Val Thr Ala Thr Ser Phe Val Ala Asn Ser Ala Thr Ile Asn Phe Gly
1               5                   10                  15

Asn Ser Leu Ala Phe Asn Ser Asn Ile Thr Gly Ser Gly Thr Thr Leu
            20                  25                  30

Thr Leu Gly Ala Asn Gln Val Thr Tyr Thr Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Asn Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110

Gly Leu Lys Pro Thr Pro Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Gly Val Ile Asp Glu Asp Phe Ala Pro
```

```
145                 150                 155                 160

Gly Gly Pro Leu Ala Asn Ile Pro Asn Ala Ala Asn Ile Lys Lys Ser
                165                 170                 175

Leu Glu Leu Met Glu Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Met Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Ala
                245                 250


<210> SEQ ID NO 20
<211> LENGTH: 250
<212> TYPE: PRT
<213> ORGANISM: Rickettsia slovaca

<400> SEQUENCE: 20

Val Thr Ala Thr Ser Phe Val Ala Asn Ser Ala Thr Ile Asn Phe Gly
1               5                   10                  15

Asn Ser Leu Ala Phe Asn Ser Asn Ile Thr Gly Ser Gly Thr Thr Leu
            20                  25                  30

Thr Leu Gly Ala Asn Gln Val Thr Tyr Thr Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Thr Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110

Gly Leu Lys Pro Thr Pro Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Asp Val Ile Asp Glu Asp Phe Ala Pro
145                 150                 155                 160

Gly Gly Pro Leu Ala Asn Ile Pro Asn Ala Ala Asn Ile Lys Lys Ser
                165                 170                 175

Leu Glu Leu Met Ala Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Met Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Ala
                245                 250


<210> SEQ ID NO 21
<211> LENGTH: 250
<212> TYPE: PRT
```

<213> ORGANISM: Rickettsia parkeri

<400> SEQUENCE: 21

```
Val Thr Ala Thr Ser Phe Val Ala Asn Ser Ala Thr Ile Asn Phe Gly
1               5                   10                  15

Asn Ser Leu Ala Phe Asn Ser Asn Ile Thr Gly Ser Gly Thr Thr Leu
            20                  25                  30

Thr Leu Gly Ala Asn Gln Val Thr Tyr Asn Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Thr Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110

Gly Leu Lys Pro Thr Pro Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Asp Val Ile Asp Lys Asp Phe Ala Pro
145                 150                 155                 160

Gly Gly Pro Leu Ala Asn Ile Pro Asn Ala Ala Asn Ile Lys Lys Ser
                165                 170                 175

Leu Glu Leu Met Gly Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Met Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Val
                245                 250
```

<210> SEQ ID NO 22
<211> LENGTH: 250
<212> TYPE: PRT
<213> ORGANISM: Rickettsia rickettsii

<400> SEQUENCE: 22

```
Val Thr Ala Thr Ser Phe Val Ala Asn Ser Ala Thr Ile Asn Phe Ser
1               5                   10                  15

Asn Ser Leu Ala Phe Asn Ser Asn Ile Thr Gly Gly Gly Thr Thr Leu
            20                  25                  30

Thr Leu Gly Ala Asn Gln Val Thr Tyr Thr Gly Thr Gly Ser Phe Thr
        35                  40                  45

Asp Thr Leu Thr Leu Asn Thr Thr Phe Asp Gly Ala Ala Lys Ser Gly
    50                  55                  60

Gly Asn Ile Leu Ile Lys Ser Gly Ser Thr Leu Asp Leu Ser Gly Val
65                  70                  75                  80

Ser Thr Leu Ala Leu Val Val Thr Ala Thr Asn Phe Asp Met Asn Asn
                85                  90                  95

Ile Ser Pro Asp Thr Lys Tyr Thr Val Ile Ser Ala Glu Thr Ala Gly
            100                 105                 110
```

-continued

```
Gly Leu Lys Pro Thr Ser Lys Glu Asn Val Lys Ile Thr Ile Asn Asn
        115                 120                 125

Asp Asn Arg Phe Val Asp Phe Thr Phe Asp Ala Ser Thr Leu Thr Leu
    130                 135                 140

Phe Ala Glu Asp Ile Ala Ala Asp Val Ile Asp Gly Asp Phe Ala Pro
145                 150                 155                 160

Gly Gly Pro Leu Ala Asn Ile Pro Asn Ala Ala Asn Ile Lys Lys Ser
                165                 170                 175

Leu Glu Leu Met Glu Asp Ala Pro Asn Gly Ser Asp Ala Arg Gln Ala
            180                 185                 190

Phe Asn Asn Phe Gly Leu Met Thr Pro Leu Gln Glu Ala Asp Ala Thr
        195                 200                 205

Thr His Leu Ile Gln Asp Val Val Lys Pro Ser Asp Thr Ile Ala Ala
    210                 215                 220

Val Asn Asn Gln Val Val Ala Ser Asn Ile Ser Ser Asn Ile Thr Ala
225                 230                 235                 240

Leu Asn Ala Arg Met Asp Lys Val Gln Ser
                245                 250
```

RECOMBINANT ANTIGENS FOR DIAGNOSIS AND PREVENTION OF SPOTTED FEVER RICKETTSIAE

CROSS-REFERENCE OF RELATED APPLICATION

This application claims priority to U.S. provisional application No. 61/059,382 filed on Jun. 6, 2008, which is hereby incorporated by reference.

BACKGROUND OF THE INVENTION

1. Field of Invention

The present invention relates to genes and proteins that can be used in vaccination, detection and identification of spotted fever rickettsiae infection. More particularly, the invention relates to specific nucleotide sequences encoding a highly specific and immunogenic portion of the outer membrane protein A (OmpA) of *Rickettsia rickettsii*. The polypeptide sequence can be utilized in diagnostic and detection assays for spotted fever rickettsiae and as an immunogen component in vaccine formulations against spotted fever *Rickettsia*.

2. Description of the Prior Art

Rickettsiae are Gram-negative, obligate intracellular parasites of the genus *Rickettsia*. They are responsible for many spotted fever group *Rickettsia* infection, and typhus group infection [1]. Of the spotted fever group, Rocky Mountain spotted fever is the most severe and most frequently reported rickettsial illness in the United States. It also occurs in Mexico and in central and south America. The disease is caused by *Rickettsia rickettsii*, a species of bacteria that is transmitted to humans by ixodid (hard) ticks. Rickettsiae target vascular endothelium. Other named species of the spotted fever group and their geographic distributions are listed in table 1.

Table 1 of Human Disease around the world caused by spotted fever group Rickettsiae. (http://www.cdc.gov/ncidod/dvrd/rmsf/Epidemiology.html, Apr. 1, 2008).

| Organism | Disease or Presentation | Geographic Location |
|---|---|---|
| *Rickettsia rickettsii* | Rocky Mountain spotted fever | North, Central and South America |
| *Rickettsia conorii* | Mediterranean spotted fever, boutonneuse fever, Israeli spotted fever, Astrakhan fever, Indian tick typhus | Europe, Asia, Africa, India, Israel, Sicily, Russia |
| *Rickettsia akari* | Rickettsialpox | Worldwide |
| *Rickettsia sibirica* | Siberian tick typhus, North Asian tick typhus | Siberia, People's Republic of China, Mongolia, Europe |
| *Rickettsia australis* | Queensland tick typhus | Australia |
| *Rickettsia honei* | Flinders Island spotted fever, Thai tick typhus | Australia, South Eastern Asia |
| *Rickettsia africae* | African tick-bite fever | Sub Saharan Africa, Caribbean |
| *Rickettsia japonica* | Japanese or Oriental spotted fever | Japan |
| *Rickettsia felis* | Cat flea rickettsiosis, flea borne typhus | Worldwide |
| *Rickettsia slovaca* | Necrosis, erythema, lymphoadenopathy | Europe |
| *Rickettsia heilongjaiangensis* | Mild spotted fever | China, Asian Region of Russia |
| *Rickettsia parkeri* | Mild spotted fever | USA |

Rocky Mountain spotted fever (RMSF) can be treated easily with antibiotics. If the patient is treated within the first 4-5 days of the disease, fever generally subsides within 24-72 hours. However, it is very difficult to make a clinical diagnosis in the disease's early stages. The early clinical presentation of Rocky Mountain spotted fever is nonspecific and may resemble a variety of other diseases including influenza, measles, and rubella, as well as other rickettsial diseases [2]. The classic symptoms of RMSF are sudden onset of fever, headache, and muscle pain, followed by development of rash, abdominal pain, joint pain, and diarrhea [2]. However, this combination of symptoms is not always detected when the patient initially presents for care. Without prompt and appropriate treatment, the disease can be fatal. Long-term health problems following acute Rocky Mountain spotted fever infection include partial paralysis of the lower extremities, gangrene requiring amputation of fingers, toes, or arms or legs, hearing loss, loss of bowel or bladder control, movement disorders, and language disorders. These complications are most frequent in persons recovering from severe, life-threatening form of the disease, often following lengthy hospitalizations. Therefore, rapid and accurate diagnosis and treatment at the onset of the disease is desirable.

Serologic assays are the most widely available and frequently used methods for confirming cases of Rocky Mountain spotted fever. The indirect immunofluoresence assay (IFA) is generally considered the reference standard in Rocky Mountain spotted fever serology and is the test currently used by Center of Disease Control and most state public health laboratories, but other well validated assays can also be used in diagnosis, including indirect hemagglutination assay (IHA), ELISA, latex agglutination, and dot immunoassays [2].

IFA can be used to detect either IgG or IgM antibodies. Blood samples taken at early (acute) and late (convalescent) stages of the disease are the preferred specimens for evaluation. Most patients demonstrate increased IgM titers by the end of the first week of illness. Diagnostic levels of IgG antibody generally do not appear until 7-10 days after the onset of illness. The value of testing two sequential serum or plasma samples together to show a rising antibody level is very important in confirming acute infection with rickettsial agents because antibody titers may persist in some individuals for years after the original exposure to cross-reactive rickettsial agents. IgG antibodies are more specific and reliable since other bacterial infections can also cause elevations in riskettsial IgM antibody titers. One of the disadvantage in using IFA to diagnose Rocky Mountain spotted fever is that most patients visit their physician relatively early in the course of the illness, before the presences of diagnostic antibody level. In addition, variations in the endpoint titer may occur due to differences in the quality of the microscope, the quality of the anti-immunoglobulin conjugate, and the experience of the technician.

Both IHA and latex agglutination rely on a common source of rickettsial antigen, extracted from *R. rickettsii*. This antigenic material is coated on sheep or human type O erythrocytes for IHA and onto latex beads for latex agglutination. Although IHA test demonstrates the earliest, steepest rise in antibody titer of all serologic tests for RMSF, it is rarely used as the diagnostic method in acute state of the illness. Only 19% of patients with RMSF had an acute titer of 40, which is much lower value than CDC's criterion for using a single titer indicating a probable diagnosis (≥128) [2]. The latex agglutination test is technically simple and rapid and requires no elaborate equipment. However, latex agglutination test is inappropriate for serosurveys and is more diagnostically discriminatory for establishing the diagnosis of a recent infection because the detectable antibody has persistent presentation months after the onset of illness [2].

Although routinely used in retrospective confirmatory diagnosis, current serologic methods are not considered appropriate rapid acute diagnostic tests. Very seldom are specific antibodies to *R. rickettsii* detected during the acute stage of illness when empiric treatment must begin. The most rapid and specific diagnostic assays for Rocky Mountain spotted fever rely on molecular methods like PCR, which can detect DNA of 5-10 rickettsial organisms in a sample. While organisms can be detected in whole blood samples obtained at the acute onset of illness in a few hours, rickettsial DNA is most readily detected in fresh skin biopsies like those used in immunostaining procedures. PCR can also be done on the fixed tissues used in immunostaining, but it is less sensitive than with unfixed tissues. PCR methods can be *R. rickettsii*-specific but are usually confirmed by DNA sequencing of the amplified gene fragments. Consequently, this procedure is more specific than antibody-based methods which are often only genus or spotted fever group-specific. However, gene amplification requires sophisticated instrumentation and reagents generally not available in most rural medical facilities. In addition, extensive training is required for the end users to achieve accurate and standardized results.

Another approach to Rocky Mountain spotted fever diagnostics is immunostaining. This method is used by taking a skin biopsy of the rash from an infected patient prior to therapy or within the first 48 hours after starting the antibiotic therapy. However, because rickettsiae are focally distributed in lesions of Rocky Mountain spotted fever, this test may not always detect an agent. Even in laboratories with expertise in performing this test, the sensitivity is only about 70% on biopsied tissues because of the scarcity of organisms in some samples.

Two major outer membrane proteins of spotted fever group Rickettsiae, OmpA and OmpB, have been identified as major immunogenic antigens. Outer membrane protein A (OmpA) has an apparent molecular mass of 190 kDa. Immunization with recombinant rOmpA (*Rickettsia* OmpA) protects guinea pigs against a lethal dose of *R. rickettsii*. The rOmpA gene of (*R. Rickettsia*) contains 6747 nucleotides that code for 2249 amino acid protein [5]. Moreover, immunization with recombinant OmpA of *R. conorii* completely protects guinea pigs against challenge with *R. conorii* and partially protects against challenge with *R. rickettsii [*6]. OmpA of *R. Rickettsii* was also shown to react strongly with sera from patients infected with *R. rickettsii* and other spotted fever group *Rickettsia*. Based on these observations, therefore, OmpA is a particularly advantageous target for developing diagnostic reagents against spotted fever group *Rickettsia*, especially against *R. Rickettsii*, the causative agent of RMSF.

FIG. 1 shows that fragment X of Omp A is conserved among various spotted fever group *Rickettsia*. FIG. 2 is a comparison of fragment Y of OmpA from various spotted fever group *Rickettsia.*

SUMMARY OF INVENTION

Accordingly, an object of this invention is recombinant polypeptides encompassing immunologic regions of OmpA of *R. Rickettsii.*

Another object of the invention is a method for using recombinant polypeptides encompassing immunologic regions of OmpA of *R. Rickettsii* in antibody-based assays for the detection of spotted fever group rickettsiae.

Yet another object of the invention is a method for using recombinant polypeptides encompassing immunologic regions of OmpA *R. Rickettsii* in vaccine formulations against spotted fever infections.

BRIEF DESCRIPTION OF DRAWINGS

FIG. 1 shows alignment of polypeptide sequences of X fragment of the OmpA ("OmpA_X") from various spotted fever group *Rickettsia*, including *R. slovaca* (SEQ ID NO: 13), *R. honei* (SEQ ID NO:14), *R. rickettsii* (SEQ ID NO: 3), *R. peacockii* (SEQ ID NO:16), *R. parkeri* (SEQ ID NO: 17).

FIG. 2 shows alignment of polypeptide sequences of the Y fragment of the OmpA ("OmpA_Y") from various spotted fever group *Rickettsia, R. conorii* (SEQ ID NO:19), *R. slovaca* (SEQ ID NO:20), *R. honei* (SEQ ID NO: 18), *R. rickettsii* (SEQ ID NO:5), *R. parkeri* (SEQ ID NO:21).

FIG. 4 Vector maps for (a) pET24a and (b) pET28a.

DETAILED DESCRIPTION OF THE INVENTION

Figure 3:
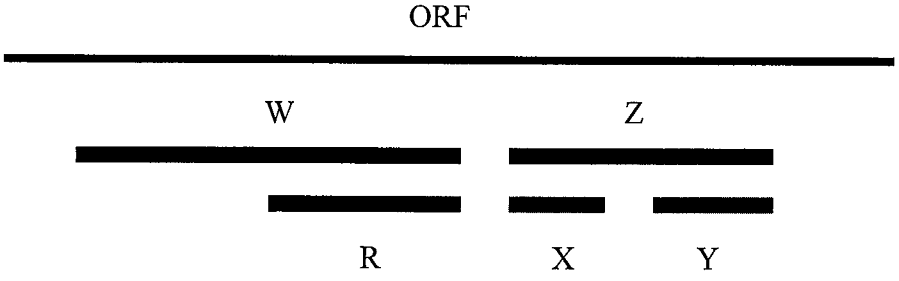
FIG. 3 Open reading frame of OmpA and location of Fragments X, Y and Z.

Study of spotted fever group *Rickettsia* has led to the identification of OmpA, which is an exceptionally promising candidate as a reagent for use in diagnostic and detection assays, as well as in vaccine formulations. Central to the development and standardization of improved detection and diagnostic immunoassay methods is the development of more effective antigens for use in antibody-based methods. With a molecular weight of 190 kDa, however, OmpA is difficult to express and purify. Therefore, the large OmpA (190 kDa), is divided into five epitope-containing fragments: W (94 kDa), R (47 kDa), X (25 kDa), Y (26 kDa), and Z (70 kDa) (FIG. 3). Each fragment can be found in a region of OmpA that is predicted to be rich in epitopes. An epitope is the region of an antigen to which the variable region of an antibody binds. Most antigens have a large number of epitopes. The purified antigens may then be used to detect antibodies against Rickettsiae caused spotted fever, and diagnose the disease. By invoking an immunogenic reaction, the antigens may also be used as vaccines. FIG. 3 illustrates the location of these fragments within the OmpA molecule. The amino acid sequence of OmpA is illustrated in SEQ ID No. 1, which is encoded by nucleotide sequence set forth in SEQ ID No. 2. Fragment X has the amino acid sequence of SEQ ID No. 3 and is encoded by nucleotide sequence set forth in SEQ ID. No. 4. Fragment Y has the amino acid sequence of SEQ ID No. 5 and is encoded by nucleotide sequence set forth in SEQ ID 6. Fragment Z is a longer fragment containing both fragment X and Y. Fragment Z's amino acid sequence is set forth in in SEQ ID 11 and is encoded by nucleotide sequence set forth in SEQ ID. 12. Rapid tests made with purified antigen for *R. rickettsii* may enable timely, accurate diagnosis of Rocky Mountain spotted fever, which can be performed even in locations where laboratory equipment is not available.

Figure 4:
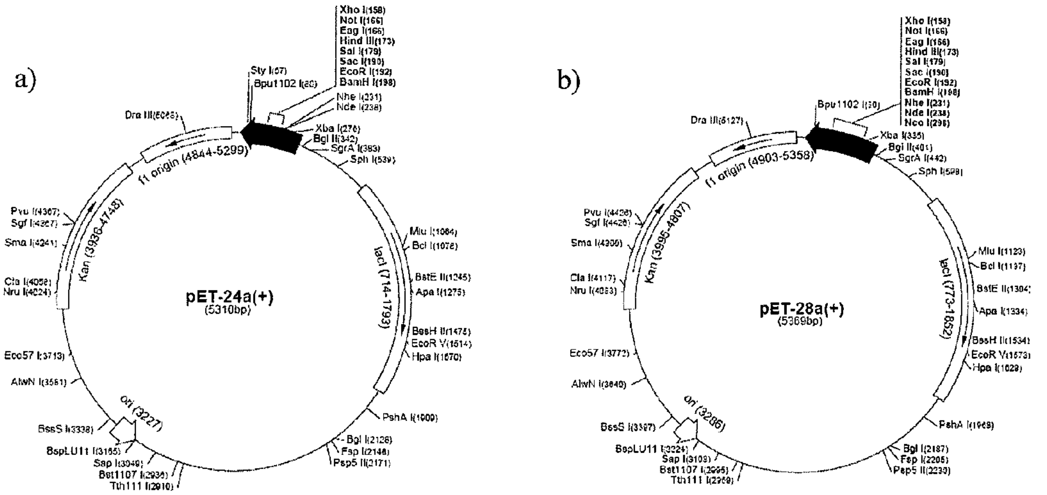

Construction of recombinant *R. rickettsia* OmpA fragments were carried out by the expression, purification, and refolding of the X, Y and Z fragments (OmpA-X, OmpA-Y and OmpA-Z). The gene coding OmpA-X (from a.a. 1281 to a.a. 1522 of OmpA) was cloned into the expression vector pET24a. The gene encoding OmpA-Y (from amino acids 1700 to 1950 of OmpA) was cloned into the expression vector pET28a. The gene encoding OmpA-Z (from amino acids 1281 to 1950) was cloned into the expression vector pET 24a. FIG. 4 shows the Vector maps for (a) pET24a and (b) pET28a. BL21(DE3) strain of *Escherichia coli* was transformed with plasmid containing gene segments for OmpA-X, OmpA-Y and Omp-Z. Following induction, the cells were lysed, and OmpA-X, OmpA-Y and Omp-Z was each found in the inclusion body. The solubilized OmpA-X, OmpA-Y and OmpA-Z in 8 M urea was purified by His-tag affinity chromatography. SDS-PAGE demonstrated that greater than 90% purity was achieved in the final elution. The purified protein fragments were refolded by sequential dialysis at 4° C. in progressively lower concentrations of urea. N-terminal protein sequencing was used to confirm the identity of the refolded proteins. Western blot experiments showed that OmpA-X, OmpA-Y and Omp-Z reacted with patient sera, OmpA-Y reacted especially strong, suggesting that these fragments can be used to develop rapid sero-diagnostic assays and may even be a candidate for a vaccine against Rocky Mountain spotted fever.

Cloning of OmpA X, Y and Z Genes into Expression Vectors

A set of oligonucleotide primers were used to amplify X and Y fragments.

TABLE 2

Primer sets for OmpA-X, OmpA-Y and OmpA-Z fragments.

| | | |
|---|---|---|
| SEQ ID No. 7 | OmAXf | GGT GGT CAT ATG CGA GAT TCT GTT TTA GTA CTT TCT |
| SEQ ID No. 8 | OmAXr | GGT GGT CTC GAG TTG AGT TAA TTG AAC AGC ATC ATT A |
| SEQ ID No. 9 | OmAYf | GGT GGT CAT ATG GTA ACG GCT ACC AGC TTT GTA G |
| SEQ ID No. 10 | OmAYr | GGT GGT CTC GAG TGA TTG TAC TTT ATC CAT TCT AGC |
| SEQ ID No. 7 | OmAZf | GGT GGT CAT ATG CGA GAT TGT GTT TTA GTA CTT TCT |

TABLE 2-continued

Primer sets for OmpA-X, OmpA-Y and OmpA-Z fragments.

| | | |
|---|---|---|
| SEQ ID No. 10 | OmAZr | GGT GGT CTC GAG TGA TTG TAC TTT ATC CAT TCT AGC |

The expression vector pET24a and pET28a were digested with NdeI and XhoI (NEW ENGLAND BIOLABS® Inc, Beverly Mass.). The PCR product for OmpA-X, OmpA-Y and Omp-Z were also digested with NdeI and XhoI. Agarose gel electrophoresis was performed with the samples. The digested vectors and the X and Y inserts were then cut out from the gel and purified using the QIAquick Gel Extraction Kit (QIAGEN™, Valencia Calif.). The vectors and inserts were ligated together with T4DNA ligase (INVITROGEN™, Carlsbad Calif.). *E. coli* TOPO10 was transform with the resulting plasmids, now pET24a-OmpA-X, pET24a-OmpA-Z and pET28a-OmpA-Y for cloning. The transformed cells were spread on agar plates that contained 50 μg/mL kanamycin and incubated overnight at 37° C. The plasmids were then purified using QIAprep Spin Miniprep Kit (QIAGEN™, Valencia Calif.). A sample of the purified DNA was subjected to a double digestion with NdeI and XhoI, and agarose gel electrophoresis was performed to verify that the inserts had been successfully ligated into the vectors. The pET28a-OmpA-Y plasmid encoded OmpA-Y with a histidine tag on both the N- and C-terminuses, and the pET24a-OmpA-X plasmid encoded OmpA-X with a histidine tag on the C-terminus. The pET24a-OmpA-Z plasmid encoded OmpA-Z with a histidine tag on the C-terminus

Expression of OmpA-X, OmpA-Y and OmpA-Z

The plasmids containing the insert were used to transform into the expression hosts. The recombinant *E. coli* were spread on agar plates containing 50 μg/mL kanamycin and were incubated at 37° C. overnight. The recombinant *E. coli* expressing the OmpA fragment was then grown in 0.5 L OVERNIGHT EXPRESS™ Instant TB Medium (NOVAGEN®, Gibbstown N.J.) containing 50 μg/mL kanamycin at 37° C. with shaking at room temperature. The medium induced protein expression. Following induction, the cells were harvested by centrifugation. The cell pellets were resuspended in 15 mL BUGBUSTER® Master Mix (NOVAGEN®, Gibbstown N.J.). The lysis reaction was allowed to proceed for 30 minutes with shaking. The cells were also subjected to ultrasonic disruption on a sonicator for further lysing. The cell lysate was then centrifuged at 7400×g for 30 minutes. The supernatant was collected and saved. The pellet was resuspended in 30 mL 1×HisBind buffer (20 mM Tris-Hcl pH 8, 0.5 M NaCl, 10 mM imidazole) and centrifuged for 30 minutes as before. The supernatant was collected and saved. This process was repeated with 30 mL 1×HisBind buffer containing 2M urea, and finally with 15 mL 1×HisBind buffer containing 8M urea. Bradford's test and sodium dodecyl sulfate polyacrylamide gel electrophoresis (SDS-PAGE) was used to analyze the fractions and determine the protein concentration of OmpA-X, OmpA-Y and OmpA-Z.

Purification of OmpA-X and OmpA-Y

Ni-NTA His-bind Resin (NOVAGEN®, Gibbstown N.J.) was used to purify OmpA fragments from the impurities in the sample. Two milliliters of the Ni-NTA His-bind resin suspension were added to make a 1 mL column. The column was equilibrated with 10 mL of 1×HisBind buffer containing 8M urea. Both OmpA-X and OmpA-Y were found in the inclusion body. The solubilized protein in 8M urea was then added to the column. After an incubation period of 30 minutes with shaking, the resin was allowed to settle. The flow-through was collected and saved. The column was washed twice with 10 mL 1×HisBind buffer containing 8 M urea. OmpA fragment was eluted with six 1 mL solutions, each with an increasing concentration of imidazole (20 mM, 50 mM, 100 mM, 200 mM, 400 mM, and 600 mM). Bradford's test was performed to determine the protein concentration of each fraction, and SDS-PAGE was used to analyze the purity of the samples.

Refolding of OmpA-X and OmpA-Y

The purified OmpA fragments in 8M urea was refolded by dialysis against progressively lower concentrations of urea (6 M, 4 M, 2 M, 1 M, 0 M, and 0 M) at 4° C. In addition to urea, each buffer contained 20 mM Tris-HCl (pH 8), 0.15 M NaCl, 1 mM dithiothreitol (DTT), and 1 mM ethylenediamine tetraacetic acid (EDTA). The D-Tube™ Dialyzer Maxi MWCO 12-14 kDa (NOVAGEN®, Gibbstown N.J.) was used for dialysis. The tube was hydrated for 30 seconds in 6M urea buffer, and then the protein sample to be refolded was added to the tube. The beaker containing the buffer and the tubes was placed on a stirrer for 1.5 hours. After this period of time, the tubes were transferred to the 4M urea buffer and left on the stirrer for 1.5 hours. This process was repeated for the rest of the buffers. After the second 0M urea buffer, the protein was recovered. Bradford's test was used to determine the protein concentration of the refolded sample.

Alternative Extraction, Purification and Refolding Procedures

To obtain OmpA fragments at a higher purity, alternative extraction, purification and refolding protocols may also be used. In this alternative embodiment, the cell pellet was well dispersed in buffer containing 20 mM Tris-HCl (pH 8), 1 mM dithiothreitol (DTT), and 1 mM ethylenediamine tetraacetic acid (EDTA), via up-down suction using a 10-ml pipette. The cells were broken using a Microfluidizer and centrifuged at 11,250×g for 30 min at 4° C. Supernatant was disgarded and 2M urea in buffer containing 20 mM Tris-HCl (pH 8), 1 mM dithiothreitol (DTT), and 1 mM ethylenediamine tetraacetic acid (EDTA) was added to the pellet. The pellets were dispensed well and spin down as described before. These steps were repeated once. The supernatant was disgarded and 6 M urea in buffer containing 20 mM Tris-HCl (pH 8), 1 mM dithiothreitol (DTT), and 1 mM ethylenediamine tetraacetic acid (EDTA) was added. The pellet was well dispersed by up-down suction using a 10-ml pipette. The solution was centrifuged at 11,250×g for 30 min at 4° C. Supernatant is collected for gel filtration purification.

Chromatographic purification of OmpA-X and OmpA-Y A were performed using gel filtration HPLC on TSK P3000SW (21.5 mm×30 cm) or TSK P4000SW (21.5 mm×60 cm) with Waters 600E and Phamarcia Recorder and monitor using a running buffer of 6 M urea, 20 mM Tris-HCl, 1 mM DTT, 1 mM EDTA, 0.15 M NaCl (pH8.0). Pre-equilibration of the TSK P3000SW in tandem with 4000SW preparative column by running the elution buffer on the column overnight (about 15 h) at a flow rate of 0.35 ml/min for 21.5 mm×30 cm column bed (about 100 ml) or at 0.65 ml/min for 21.5×60 cm column bed (208 ml). Isocratic elution run and fractionation were conducted on the sample with 6M urea solution loaded into a 5 ml loop at a flow rate of 4 ml/min. Fractionations were collected at the beginning of peak appearance and analyzed by gel electrophoresis for purity check.

Ni-NTA purification were then performed using Hisbind buffer containing 20 mM TrisHCl, 0.5 M NaCl, 10 mM imidazole, 8M Urea (pH 8.0). Fractions containing fragments of higher purity were pooled, and dialyzed for 30 minutes against 8M Urea in buffer containing 20 mM Tris-HCl (pH 8), 1 mM dithiothreitol (DTT), and 1 mM ethylenediamine tetraacetic acid (EDTA) and 0.5M NaCl twice at room temperature. The volume ratio of sample to buffer is 0.02 (i.e. 1 ml sample 50 ml buffer). Sample was loaded onto 1 ml of Ni-NTA (NOVAGEN®, Gibbstown N.J.) column equilibrated with 10 ml Hisbind buffer. The sample was allowed the binding to perform for 15 min at RT with rocking. Collected flow-through samples and washed column with 20 ml Hisbind buffer. Proteins were then eluted with 6×1.0 ml of Hisbind buffer containing 25 mM, 50 mM, 100 mM, 200 mM, 500 mM, and 1M imidazole. Major protein appeared in fractions containing 50 to 200 mM imidazole. Check the elution purity in 4-20% SDS gel.

Chromatographic purification of OmpA-Z was performed in 6M urea buffer using an Anion-exchange HPLC on a Waters preparative DEAE column (21.5×15 cm, max. binding capacity, approx 700 mg protein) with Waters 2196 HPLC system interfaced with Millenium software. The starting buffer is 6M urea in 20 mM Tris-HCl (pH 8.0). The second buffer is 6 M urea in 0.5 M NaCl in 20 mM Tris-HCl (pH 8.0). The ending buffer is 6 M urea in 2 M NaCl in 20 mM Tris-HCl (pH 8.0). All buffers also contain 1 mM DTT, 1 mM EDTA, 20 M Tris-HCl (pH 7.5, Fisher). Pre-washing and equilibration were performed on DEAE column followed by fractionation at 0.15 min per fraction. Run SDS-4-20% Tris-HCl bio-rad ready gel BIO-RAD® Laboratories, Hercules, Calif.) to check the fractions. Poll the relative pure fractions for Ni-NTA column purification.

Ni-NTA column purification was conducted using HIS-BIND® buffer containing 20 mM TrisHCl, pH 8.0, 0.5 M NaCl, 10 mM imidazole, 8M Urea. Fractions containing fragments of higher purity were pooled and dialyzed for 30 minutes against 8M Urea in buffer containing 20 mM Tris-HCl (pH 8), 1 mM dithiothreitol (DTT), 1 mM ethylenediamine tetraacetic acid (EDTA) and 0.5M NaCl in Tris buffer pH8.0 twice at room temperature. The volume ratio of sample to buffer is 0.02 (i.e. 1 ml sample 50 ml buffer). Dialyzed sample was mixed with 1 ml of Ni-NTA (NOVAGEN®, Gibbstown N.J.) column previously equilibrated with 10 ml Hisbind buffer. The mixture was rocking at room temperature for 15 minutes. The flow-through samples were then collected and washed column with 20 ml Hisbind buffer. Proteins were eluted with 6×1.0 ml of Hisbind buffer containing 25 mM, 50 mM, 100 mM, 200 mM, 400 mM, and 1M imidazole. The majority of OmpA-Z appeared in fractions containing 50 to 200 mM imidazole.

The purified OmpA polypeptide fragments (OmpA-X, OmpA-Y and OmpA-Z) were then refolded by dialysis against progressively lower concentrations of urea (4M, 2M, 1 M, and 0 M) at 4° C. in buffer containing 20 mM Tris-HCl (pH 8), 0.15 M NaCl, 1 mM DTT, and 1 mM EDTA (900 ml). The sample was dialyzed against 4 M urea for 30 minutes in buffer containing 20 mM Tris-HCl (pH 8), 1 mM dithiothreitol (DTT), and 1 mM ethylenediamine tetraacetic acid (EDTA) twice in cold room. The volume ratio of sample to buffer is 0.05 (i.e. 1 ml sample 20 ml buffer). After dialysis in 0 M urea buffer, the protein was recovered and analyzed by BioRad protein assay and by SDS gel electrophoresis.

Example 1

Figure 5:
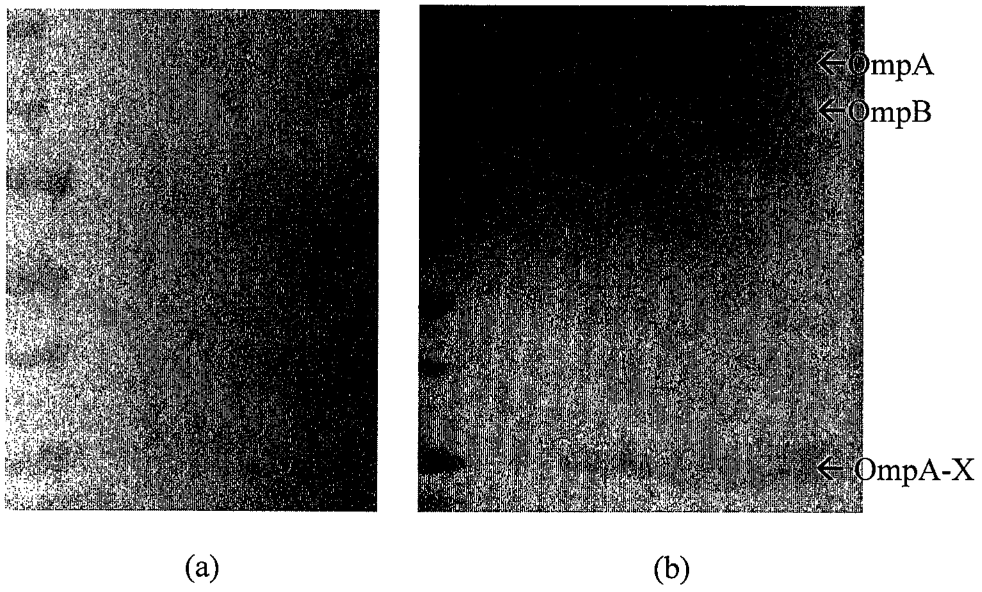
FIG. 5A Western blot analysis of OmpA, OmpB, and Fragment X with normal serum.
FIG. 5B Western blot analysis of OmpA, OmpB, Fragment X with patient serum.
Figure 6:
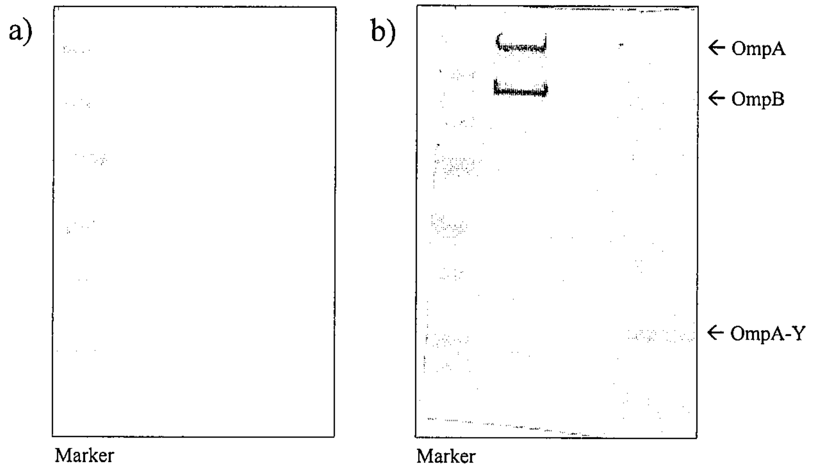
FIG. 6A Western blot analysis of OmpA, OmpB, and Fragment Y with normal serum.
FIG. 6B Western blot analysis of OmpA, OmpB, and Fragment Y with patient serum.
Figure 7:
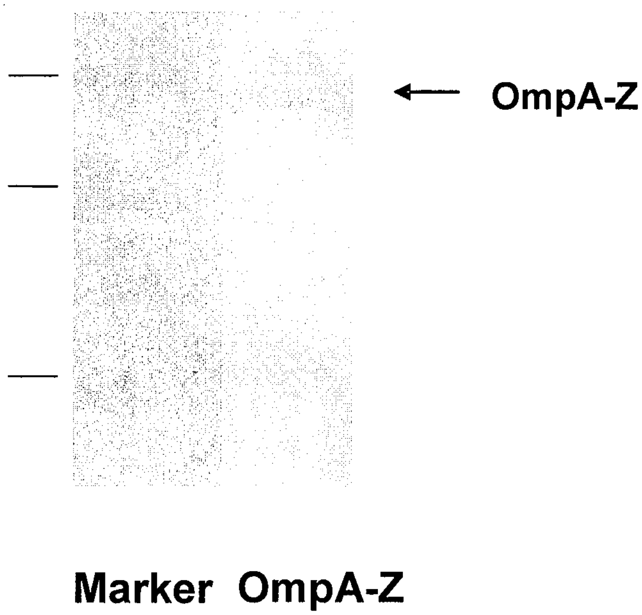
FIG. 7 Western blot analysis of Fragment Z with normal (a) serum, and patient serum (b).

Western Blot Experiment Demonstrating Immunogenic Reactivity of Fragments X, Y and Z In order to ascertain the reactivity of the recombinant Fragments X, Y and Z as immunogenic antigens for Rocky Mountain spotted fever, western blot analysis was performed on Fragments X, Y and Z of OmpA of R. *Rickettisia* using normal sera and sera from patient who are known to be spotted fever positive. The purified and refolded proteins were subjected to SDS-PAGE and then electroblotted onto a nitrocellulose membrane (BIO-RAD® Laboratories, Hercules, Calif.). The entire procedure was carried out at room temperature. The membrane was blocked for non-specific binding by incubating with 10% skim milk in 1×TBS buffer for 1 hour with rocking. The milk was then poured off, and the membrane was washed once with 1×TBST buffer. Patient sera containing the primary antibody was diluted 100-fold in 1×TBST containing 5% milk. The membrane was incubated with the solution for 1 hour with rocking. Next, the membrane was washed three times with 1×TBST for ten minutes each, and the secondary antibody (goat anti-human IgG Horseradish Peroxidase Conjugate, 1:4000 dilution in 1×TBST). After 1 hour, the membrane was washed with 1×TBST. Three milliliters of OPTI-4CN Substrate were added to detect antibodies. After 10 minutes, the membrane was washed with water. FIG. 5 illustrates the specificity of the recombinant Fragment X by western blot analysis. In FIG. 5 (*a*), no reactivity was observed against OmpA, OmpB or Fragment X using control sera. However, OmpA and B and Fragment X are identifiable using patient sera (Panel B). FIG. 6 illustrates the specificity of the recombinant Fragment Y by western blot analysis. In FIG. 6 (*a*), no reactivity was observed against OmpA, OmpB or Fragment Y using control sera. However, OmpA and B and Fragment Y are clearly identifiable using patient sera (Panel B). FIG. 7 illustrates the specificity of the recombinant Fragment Z by western blot analysis.

Example 2

Use of OmpA Fragments X, Y and Z as Diagnostic Reagent

Assays using the recombinantly produced proteins include antibody-based assays such as enzyme-linked immunosorbent assays. As an illustration, the following procedure is provided, comprising the following steps:

1. Recombinant proteins represented by SEQ ID No. 3, 5 or 11 are immobilized, such as in 96-well plates. Alternatively, for increased sensitivity and specificity of the assay, both of the recombinant proteins represented by SEQ ID No. 3, 5 or 11 can be included together or immobilized separately but used in the same assay;
2. Wash off unreacted/unbound antigen. A preferred embodiment of the inventive method is to wash at least 3 times with wash buffer containing 0.1% polysorbate surfactant such as polyoxyethylene (20) sorbitan monolaurate;
3. Block unreacted sites. In a preferred embodiment, blocking of unreacted sites is accomplished with 5% skim milk in wash buffer)×45 minutes and then rinsed three times.
4. React test sera to the bound antigen;
5. Plates are washed three times with wash buffer;
6. After incubating the test sera, the bound antibody-antigen is exposed to a probe. In a preferred embodiment, the probe is enzyme-labeled (e.g. peroxidase) anti-human immunoglobulin;
7. detecting bound probe. Detection of bound probe can be by any number of methods. In a preferred embodiment, detection is by measurement of enzymatic reaction of added substrate.

The above specific procedural outline is provided to illustrate the general method of using the fragments for the detection spotted fever group of *Rickettsia* infection, such as a *R. Rickettsii* infection. However, other iterations of the general procedure can be contemplated. Furthermore, a standard curve can be constructed by conducting antibody-base the above ELISA procedures with the recombinant proteins but utilizing a range of concentrations of specific antibody to *R. rickettsii*. The extent of measured binding of patient serum antibody is compared to a graphic representation of the binding of the *R. rickettsii*-specific antibody concentrations.

Figure 8:
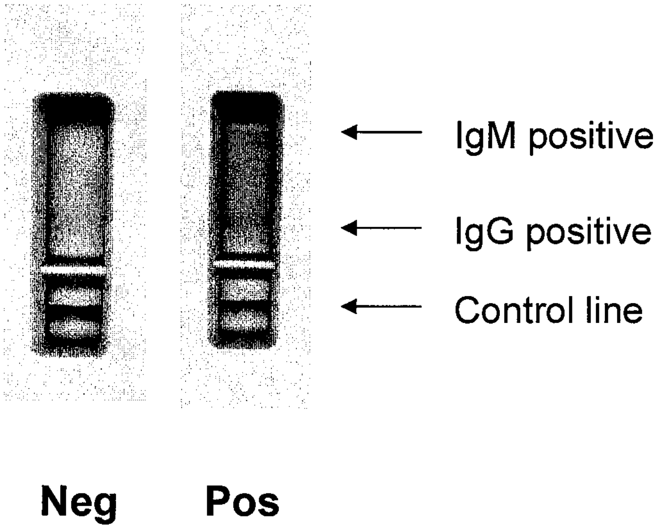
FIG. 8 Prototype SFG test assay made with OmpA-X and Y proteins.

A prototype test using OmpA-X and OmpA-Y was build and its result is shown in FIG. 8.

Example 3

Prophetic Use of Recombinant *R. Rickettisii* OmpA Fragments X and Y as a Vaccine Component The recombinantly produced polypeptides, because of their immunoreactivity to antibody in patient sera are excellent vaccine candidates. Accordingly, all or a fragment of the *R. rickettsii* proteins: Fragment X, Fragment Y or Fragment Z (SEQ ID No. 3, 5 or 11 respectively), or their respective DNA sequences (SEQ ID No. 4, 6, 12 respectively) incorporated into a suitable expression vector system, can be utilized as vaccine components. The method for induction of *R. rickettsii* immunity contains the following steps:

a. administering an immunogenic composition in a unit dose range of 50 μg to 2 mg, said immunogenic composition contains the entire or an immunogenic fragment of OmpA fragments X, Y or Z their amino acid sequences are set forth in SEQ ID No. 3, 5 or 11 respectively;
b. administration of boosting dose of said immunogenic composition at least 1 week after priming dose with unit dose range of 50 μg to 2 mg in a buffered aqueous solution, wherein an immune response is elicited.

An alternative method of immunizing is to administer DNA sequences encoding Fragments X, Y, or combinations thereof, inserted into a suitable expression system capable of expressing the fragments in vivo. Suitable expression systems can include viral expression vectors as well as a number of available DNA vector systems.

REFERENCE

1. Kelly D J, Richards A L, Temenak J, Strickman S, Dasch G A. The past and present threat of rickettsial diseases to military medicine and international public health. Clinical Infectious Diseases 2002; 34(Suppl 4):S145-69.
2. Walker D H. Rocky Mountain spotted fever: A disease in need of microbiological concern. Clinical Microbioloy Reviews 1989; 2(3):227-240.
3. Diaz-Montero C M, Feng H M, Crocquet-Valdes P A, Walker D H. Identification of protective components of two major outer membrane proteins of spotted fever group rickettsiae. American Journal of Medical Tropical Hygiene 2001; 65(4):371-378.

4. Croquet-Valdes P A, Díaz-Montero C M, Feng H M, Li H, Barrett A D T, Walker D H. Immunization with a portion of rickettsial outer membrane protein A stimulates protective immunity against spotted fever rickettsioses. Vaccine 2002; 20:979-988.
5. John W. Sumner, Kim G. Sims, Dana C. Jones and Burt E. Anderson. Protection of guinea-pigs from experimental Rocky Mountain spotted fever by immunization with baculovirus-expressed *Rickettsia rickettsii* rOmpA protein. Vaccine 1995; 13:29-35.
6. Vishwanath S, McDonald G A, Watkins N G. A recombinant *Rickettsia conorii* vaccine protects guinea pigs from experimental boutonneuse fever and Rocky Mountain spotted fever. Infect Immun 1990. 58:646-653.
7. R L Anacker, R E Mann, and C Gonzales. Reactivity of monoclonal antibodies to *Rickettsia rickettsii* with spotted fever and typhus group rickettsiae. J. Clin. Microbiol. 1987 25: 167-171.
8. R L Anacker, G A McDonald, R H List, and R E Mann. Neutralizing activity of monoclonal antibodies to heat-sensitive and heat-resistant epitopes of *Rickettsia rickettsii* surface proteins. Infect. Immun. 1987 55: 825-827.

What is claimed is:

1. An immunogenic composition comprising an isolated polypeptide fragment of outer membrane protein A (OmpA) of *Rickettsia rickettsii*, wherein said polypeptide fragment of said OmpA is selected from the group consisting of fragment X consisting of the amino acid sequence of SEQ ID NO: 3 encoded by the nucleotide sequence of SEQ ID NO: 4, fragment Y consisting of the amino acid sequence of SEQ ID NO: 5 encoded by the nucleotide sequence of SEQ ID NO: 6, fragment Z consisting of the amino acid sequence of SEQ ID NO: 11 encoded by the nucleotide sequence of SEQ ID NO: 12, and a combination thereof.

2. The immunogenic composition of claim 1, wherein said polypeptide fragment consists of the amino acid sequence of SEQ ID NO: 5.

3. The immunogenic composition of claim 1, wherein said polypeptide fragment consists of the amino acid sequence of SEQ ID NO: 3.

4. The immunogenic composition of claim 1, wherein said polypeptide fragment consists of the amino acid sequence of SEQ ID NO: 11.

5. The immunogenic composition of claim 1, wherein said composition comprises the combination of the fragment X, the fragment Y, and the fragment Z.

6. The immunogenic composition of claim 1, wherein the polypeptide fragment is purified.

7. The immunogenic fragment of claim 1, wherein the polypeptide fragment is native or recombinant.

8. A method of detecting Rocky Mountain spotted fever due to *Rickettsia rickettsii* comprising the steps of:

(a) obtaining a serum sample from a patient having the Rocky Mountain spotted fever;

(b) exposing said sample to an isolated or purified polypeptide fragment of outer membrane protein A (OmpA) reagent of *Rickettsia rickettsii*, wherein said polypeptide fragment of said OmpA reagent is selected from the group consisting of fragment X consisting of the amino acid sequence of SEQ ID NO: 3 encoded by the nucleotide sequence of SEQ ID NO: 4, fragment Y consisting of the amino acid sequence of SEQ ID NO: 5 encoded by the nucleotide sequence of SEQ ID NO: 6, fragment Z consisting of the amino acid sequence of SEQ ID NO: 11 encoded by the nucleotide sequence of SEQ ID NO: 12, and a combination thereof;

(c) incubating said sample to form a complex; and (d) allowing binding of a detectable label to the complex and detecting the detectable signal produced.

9. The method of claim 8, wherein the polypeptide fragment is immobilized prior to the exposure to the serum sample.

10. A method of inducing an immune response against Rocky Mountain spotted fever due to *Rickettsia rickettsii* comprising administering the immunogenic composition of claim 1 in a unit dose of 50 micrograms to 1 mg.

11. The method of claim 10, which further comprises administering a boosting dose of the immunogenic composition of claim 1 at least one week after a priming dose in the range of 50 micrograms to one mg, wherein the immune response is elicited.

* * * * *